US009765304B2

(12) United States Patent
Klatzmann et al.

(10) Patent No.: US 9,765,304 B2
(45) Date of Patent: *Sep. 19, 2017

(54) SYNTHETIC VIRUSES AND USES THEREOF

(71) Applicant: L'Universite Pierre Et Marie Curie, Paris (FR)

(72) Inventors: David Klatzmann, Paris (FR); Jean-Loup Salzmann, Paris (FR); Bertrand Bellier, Paris (FR); Charlotte Fribert, Paris (FR); Francois-Loic Cosset, Lyons (FR)

(73) Assignee: L'Universite Pierre Et Marie Curie, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/163,315

(22) Filed: Jan. 24, 2014

(65) Prior Publication Data
US 2014/0255445 A1    Sep. 11, 2014

Related U.S. Application Data

(63) Continuation of application No. 10/415,242, filed as application No. PCT/EP01/12356 on Oct. 25, 2001, now Pat. No. 8,673,212.

(30) Foreign Application Priority Data

Oct. 26, 2000 (EP) .................................... 00402978

(51) Int. Cl.
C12N 7/00      (2006.01)
A61K 39/12     (2006.01)
C12N 15/86     (2006.01)
A61K 39/21     (2006.01)
A61K 39/00     (2006.01)

(52) U.S. Cl.
CPC ............... C12N 7/00 (2013.01); A61K 39/12 (2013.01); A61K 39/21 (2013.01); C12N 15/86 (2013.01); A61K 2039/5258 (2013.01); C12N 2740/13023 (2013.01); C12N 2740/13043 (2013.01); C12N 2740/16122 (2013.01); C12N 2760/10034 (2013.01); C12N 2810/6072 (2013.01)

(58) Field of Classification Search
CPC .... A61K 2300/00; A61K 38/00; A61K 39/12; A61K 39/21; A61K 2039/5258; A61K 2039/525; A61K 2039/5254; A61K 38/162; A61K 39/42; C12N 7/00; C12N 15/86; C12N 2740/16034; C12N 2740/16051; C12N 2740/16234; C12N 2750/14151; C07K 14/005
See application file for complete search history.

(56) References Cited

U.S. PATENT DOCUMENTS

| 4,918,166 | A  | 4/1990  | Kingsman et al. |
| 5,580,773 | A  | 12/1996 | Kang et al. |
| 5,843,432 | A  | 12/1998 | Klatzmann et al. |
| 5,955,342 | A  | 9/1999  | Rovinski et al. |
| 6,099,847 | A  | 8/2000  | Tobin et al. |
| 6,132,731 | A  | 10/2000 | Kingsman |
| 6,140,114 | A  | 10/2000 | Klatzmann et al. |
| 6,489,142 | B1 | 12/2002 | Torrent et al. |
| 7,378,515 | B2 | 5/2008  | Wagner et al. |
| 8,287,881 | B2 | 10/2012 | Wagner et al. |
| 2005/0227224 | A1 | 10/2005 | Tangy et al. |
| 2006/0013826 | A1 | 1/2006  | Tangy et al. |
| 2006/0222661 | A1 | 10/2006 | Bartosch et al. |

FOREIGN PATENT DOCUMENTS

| DE | 19752855 A1 * | 7/1999 |
| DE | 19752855 A1   | 7/1999 |
| WO | WO-98/46083 A1 | 10/1998 |
| WO | WO-2006103493 A1 | 10/2006 |

OTHER PUBLICATIONS

Maurice M, Mazur S, Bullough FJ, Salvetti A, Collins MK, Russell SJ, Cosset FL. Efficient gene delivery to quiescent interleukin-2 (IL-2)-dependent cells by murine leukemia virus-derived vectors harboring IL-2 chimeric envelope glycoproteins. Blood. Jul. 15, 1999;94(2):401-10.*

McGuigan LC, Stallard V, Roos JM, Payne LG. Recombinant-expressed virus-like particle pseudotypes as an approach to vaccine development. Vaccine. 1993;11(6):675-8. PubMed PMID: 8322492.*

Miletic H, Bruns M, Tsiakas K, Vogt B, Rezai R, Baum C, Kühlke K, Cosset FL, Ostertag W, Lother H, von Laer D. Retroviral vectors pseudotyped with lymphocytic choriomeningitis virus. J Virol. Jul. 1999;73(7):6114-6.*

Finkelshtein D, Werman A, Novick D, Barak S, Rubinstein M. LDL receptor and its family members serve as the cellular receptors for vesicular stomatitis virus. Proc Natl Acad Sci U S A. Apr. 30, 2013;110(18):7306-11. Epub Apr. 15, 2013.*

Henderson, R.A. et al., Retroviral Expression of MUC-1 Human Tumor Antigen with Intact Repeat Structure and Capacity to Elicit Immunity in Vivo, Journal of Immunotherapy, 21(4): 247-256 (1998).

Bellier et al., DNA vaccines encoding retrovirus-based virus-like particles induce efficient immune responses without adjuvant, Vaccine 24:2643-2655 (2006).

(Continued)

Primary Examiner — Rachel B Gill
(74) Attorney, Agent, or Firm — Choate, Hall & Stewart LLP; Brenda Herschbach Jarrell; Rolando Medina

(57) ABSTRACT

The present invention relates to compositions and methods for producing an immune response or reaction, as well as to vaccines, kits, processes, cells and uses thereof. This invention more particularly relates to compositions and methods of using a synthetic viral particle to produce, modify or regulate an immune response in a subject. In a more preferred embodiment, the invention is based, generally, on compositions using synthetic viral particles as an adjuvant and/or vehicle to raise an immune response against selected antigen(s) or epitopes, in particular a cellular and/or a humoral immune response.

15 Claims, 10 Drawing Sheets

(56) References Cited

OTHER PUBLICATIONS

Figure 1:
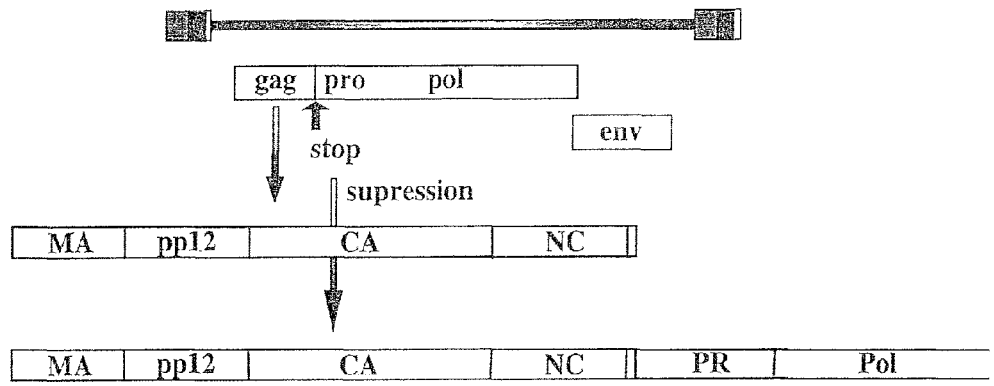
Figure 1:
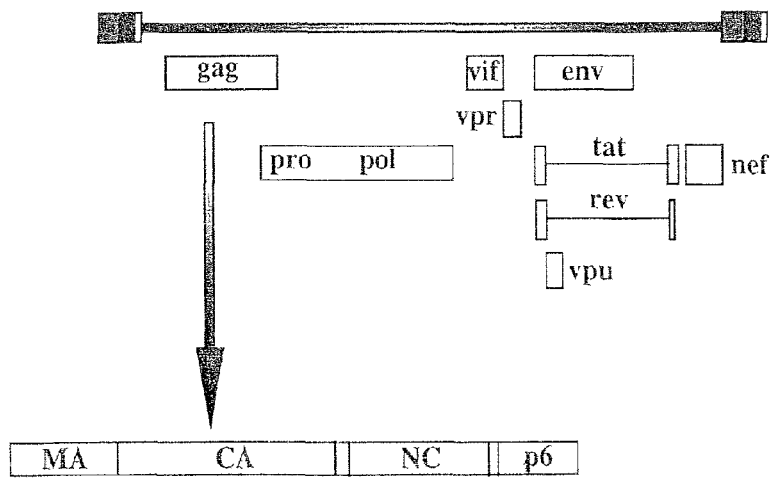

Bellier et al., DNA vaccines expressing retrovirus-like particles are efficient immunogens to induce neutralizing antibodies, Vaccine, 27:5772-5780 (2009).
Bennett et al., Conditions for Copackaging Rous Sarcoma Virus and Murine Leukemia Virus Gag Proteins during Retroviral Budding, Journal of Virology, 73(3):2045-2051 (1999).
Burns et al., Vesicular stomatitis virus G glycoprotein pseudotyped retroviral vectors: Concentration to very high titer and efficient gene transfer into mammalian and nonmammalian cells, Proc. Natl. Acad. Sci. USA, 90:8033-8037 (1993).
Chu et al., Cell targeting with retroviral vector particles containing antibody-evelope fusion proteins, Gene Therapy, 1(5):292-299 (1994).
Dalba et al., Replication-competent vectors and empty virus-like particles: new retroviral vector designs for cancer gene therapy or vaccines, Mol. Ther., 15(3):457-466 (2007).
Delchambre et al., The GAG precursor of simian immunodeficiency virus assembles into virus-like particles, EMBO J., 8(9):2653-2660 (1989).
Deml et al., Increased incorporation of chimeric human immunodeficiency virus type 1 gp120 proteins into Pr55gag virus-like particles by an Epstein-Barr virus gp220/350-derived transmembrane domain, Virology, 235(1):10-25 (1997).
Deml et al., Recombiant human immunodeficiency Pr55gag virus-like particles presenting chimeric envelope glycoproteins induce cytotoxic T-cells and neutralizing antibodies, Virology, 235(1):26-39 (1997).
Deml et al., Recombinant HIV-1 Pr55gag virus-like particles: potent stimulators of innate and acquired immune responses, Mol. Immunol., 42(2):259-277 (2005).
File History of U.S. Appl. No. 10/527,422 obtained from U.S. PTO Public Pair IFW May 30, 2007.
File History of U.S. Appl. No. 11/013,786 obtained from U.S. PTO Public Pair IFW May 30, 2007.
File History of U.S. Appl. No. 11/014,842 obtained from U.S. PTO Public Pair IFW May 30, 2007.
Gheysen et al., Assembly and release of HIV-1 precursor Pr55gag virus-like particles from recombinant baculovirus-infected insect cells, Cell, 59(1):103-112 (1989).
Hatziioannou, T., Incorporation of fowl plague virus hemagglutinin into murine leukemia virus particles and analysis of the infectivity of the pseudotyped retroviruses, Journal of Virology, 72(6):5313-5317 (1998).
Jennings et al., Designing Recombinant Vaccines with Viral Properties: A Rational Approach to More Effective Vaccines, Current Molecular Medicine, 7(2):1-13 (2007).
Jones et al., Assembly of gag-4-Galactosidase Proteins into Retrovirus Particles, Journal of Virology, 64(5):2265-2279 (1990).
Jones et al., Assembly of gag-beta-Galactosidase Proteins into Retrovirus Particles, Journal of Virology, 64(5):2265-2279 (1990).
Kang et al., Development of HIV/AIDS Vaccine Using Chimeric gag-env Virus-Like Particles, Biol. Chem., 380:353-364 (1999).
Karacostas et al., Human immunodeficiency virus-like particles produced by a vaccinia virus expression vector, Proc. Natl. Acad. Sci. USA, 86(22):8964-8967 (1989).
Kayman et al., The hyperviriable domain of the murrain leukemia virus surface protein tolerates large insertions and deletions enabling development of a retroviral particle display system, Journal of Virology, 73(3):1802-1808 (1999).
Kondo et al., The p6gag Domain of Human Immunodeficiency Virus Type 1 is Sufficient for the Incorporation of Vpr into Herologous Viral Particles, Journal of Virology, 69(5):2759-2764 (1995).
Maurice et al., Efficient Gene Delivery to Quiescent IL2-Dependent Cells by MLV-Derived Vectors Harboring IL2 Chimeric Envelopes Glycoproteins, Blood, 94(2):401-410 (1999).
McGuigan et al., Recombinant-expressed virus-like particle pseudotypes as an approach to vaccine development, Vaccine, 11(6):675-677 (1993).
Miletic et al., Retroviral Vectors Pseudotyped with Lymphocytic Choriomeningitis Virus, Journal of Virology, 73(7):6114-6116 (1999).
Sharma et al., Noninfectious virus-like particles produced by Moloney murine leukemia virus-based retrovirus packaging cells deficient in viral envelope become infectious in the presence of lipofection reagents, Proc. Natl. Acad. Sci. USA, 94(20):10803-10808 (1997).
Szecsi et al., Induction of neutralising antibodies by virus-like particles harbouring surface proteins from highly pathogenic H5N1 and H7N1 influenza viruses, Virology Journal, 3:70 (pp. 1-7) (2006).
Tobin et al., Immunologic and Ultrastructural Characterization of HIV Pseudovirions Containing Gag and Env Precursor Proteins Engineered in Insect Cells, Methods, 10:208-218 (1996).
Van Brocklin et al., Expression of Murine Leukemia Virus Gag-Escherichia coli RNase HI Fusion Polyprotein Significantly Inhibits Virus Spread, Journal of Virology, 71(4):3312-3318 (1997).
van Rensen, A., Liposomes with incorporated MHC class II/peptide complexes as antigen presenting vesicles for specific T cell activation, Pharmaceutical Research, 16(2):198-204 (1999).
Wagner et al., Studies of processing, particle formation, and immunogenicity of the HIV-1 gag gene product, Archives of Virology, 127:117-137 (1992).
Weldon et al., Incorporation of chimeric gag protein into retroviral particles, Journal of Virology, 64(9):4169-4179 (1990).
Wills, J.W., Retro-secretion of recombinant proteins, Nature, 340:323-324 (1989).
Wilson et al., Formation of Infectious Hybrid Virions with Gibbon Ape Leukemia Virus and Human T-Cell Leukemia Virus Retroviral Envelope Glycoproteins and the gag and pol Proteins of Moloney Murine Leukemia Virus, Journal of Virology, 63(5):2374-2378 (1989).
Cosset, F.-L. et al., High-Titer Packaging Cells Producing Recombinant Retroviruses Resistant to Human Serum, Journal of Virology, 69(12): 7430-7436 (1995).

\* cited by examiner

A: MLV

B: HIV-1

Retroviral genome

Without

With (Oncoretroviral, Lentiviral, Spumaviral,...)      WT      Modified

LTR    wt or modified (i.e. cell specific)       

Ψ +/-      

gag +/- wt or modified (i.e. + epitope)      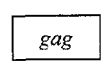 

pol +/-      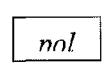

env +/- wt or modified      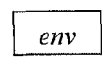 

X +/-    additional genes; wt or modified      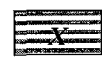 

Polypeptide gene(s)

Antigenic molecule
     WT or modified protein retaining tertiary structure
     Epitope      

Immunomodulator
     (i.e. Ils, IFN, B7....)      

Palliative
     (i.e. TK)      

Gene of Interest
     (i.e. tag, single chain Ab for targeting or purification)      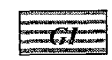

Figure 5 (Cont'd)

Figure 5:
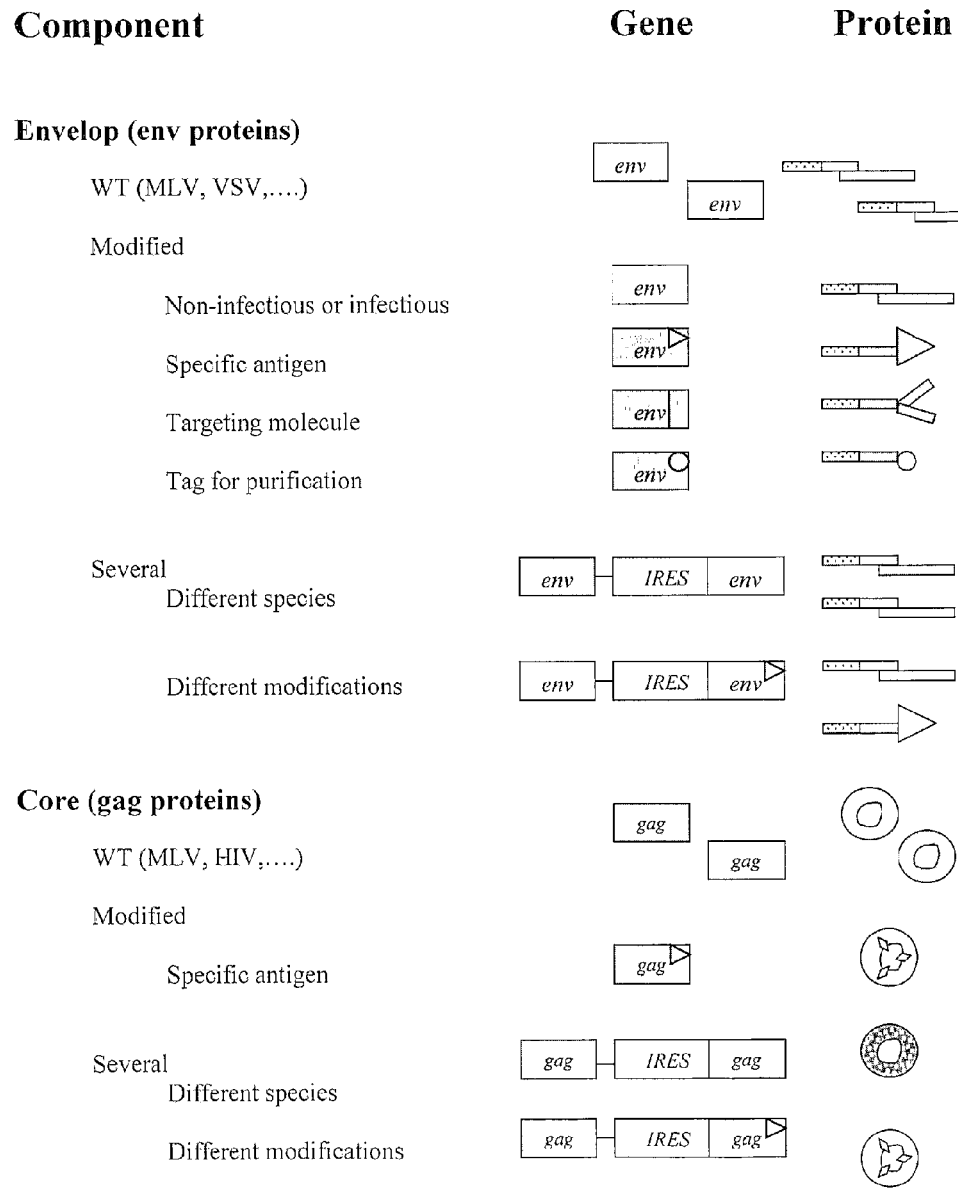

Envelop Proteins
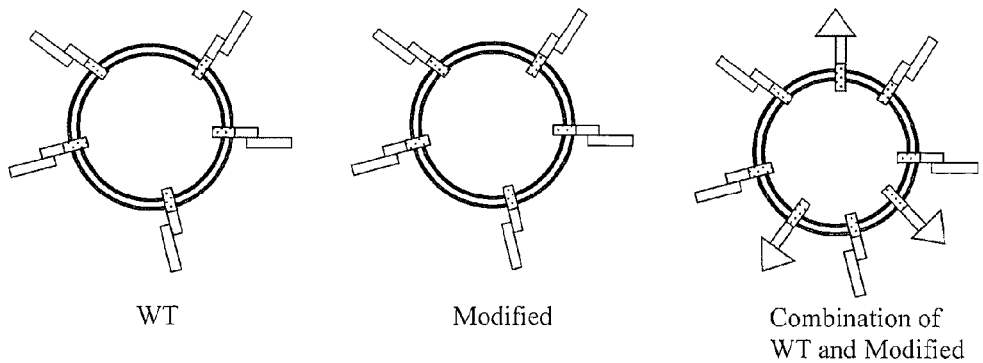
WT          Modified          Combination of
                              WT and Modified
Core Proteins
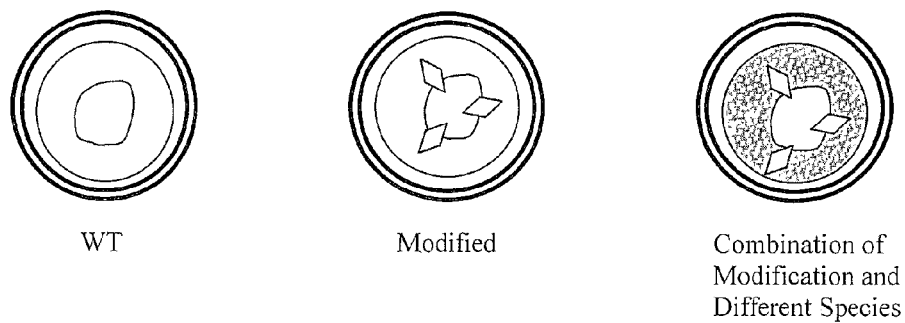
WT          Modified          Combination of
                              Modification and
                              Different Species
Retroviral Genomes
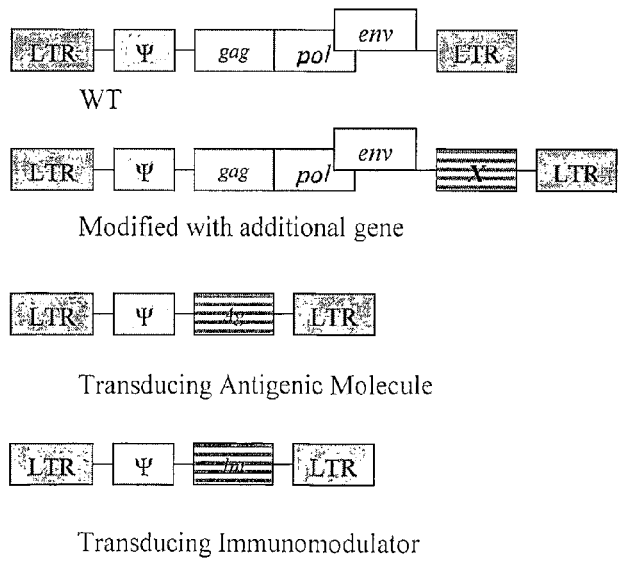
WT
Modified with additional gene
Transducing Antigenic Molecule
Transducing Immunomodulator
Figure 5 (Cont' d)

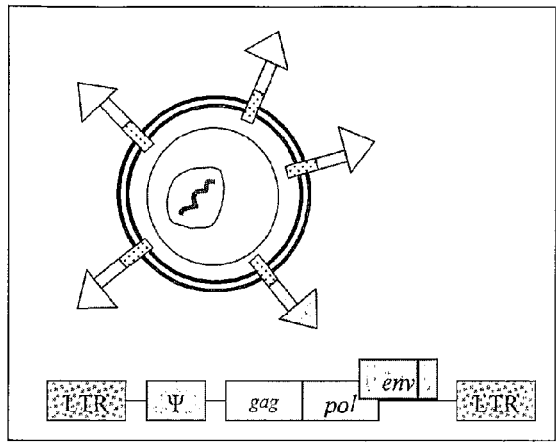

Infectious, tissue specific, replicative particle with modified envelop and WT core proteins, transducing a modified retroviral genome 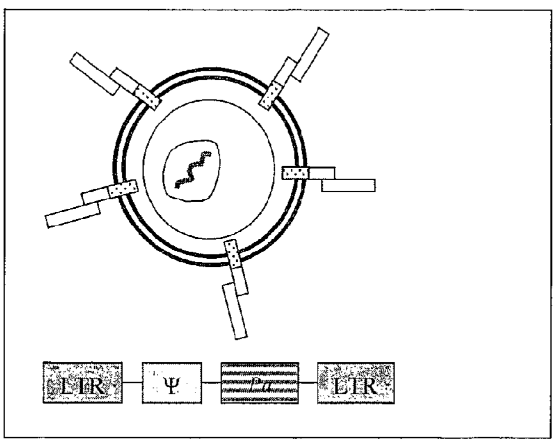 Infectious, non-replicative particle with modified envelop and core proteins,
transducing a modified retroviral genome coding for a palliative protein 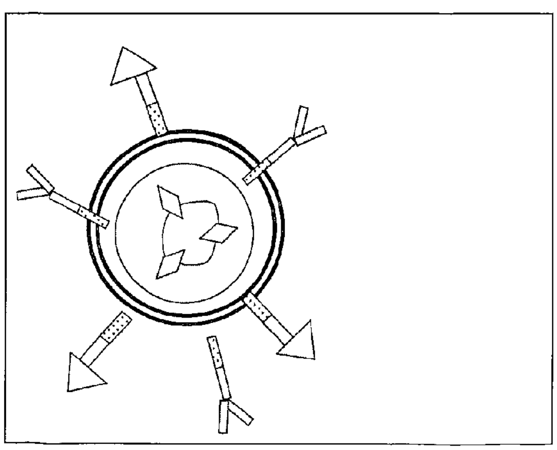 Non-infectious, non-replicative, non-transducing particle with two different modified envelop proteins and modified core proteins

SYNTHETIC VIRUSES AND USES THEREOF

CROSS-REFERENCE TO RELATED APPLICATIONS

This application is a continuation of U.S. application Ser. No. 10/415,242, filed Oct. 15, 2003, which was the National Stage of International Application No. PCT/EP01/12356, filed Oct. 25, 2001, which claims the benefit of European Application No. 00402978.1, filed Oct. 26, 2000, the entire contents of each of which are incorporated herein by reference.

The specification includes a Sequence Listing in the form of an ASCII compliant text file named "2015-10-14 Sequence Listing.txt", which was created on Oct. 14, 2015 and has a size of 2,074 bytes, the contents of which are hereby incorporated by reference in their entirety.

The present invention relates to compositions and methods for producing an immune response or reaction, as well as to vaccines, kits, processes, cells and uses thereof. This invention more particularly relates to compositions and methods of using a synthetic viral particle to produce, modify or regulate an immune response in a subject. In a more preferred embodiment, the invention is based, generally, on compositions using synthetic viral particles as an adjuvant and/or vehicle to raise an immune response against selected antigen(s) or epitopes, in particular a cellular and/or a humoral immune response.

The invention may be used in mammalian species, including human, or other vertebrate species (birds, etc.) to produce an immune response to a variety of antigens, including tumor antigens, viral antigens, pathogenic agents, cells, etc.

Various strategies have been proposed in the art to raise an immune response in a subject, such as direct administration of an antigen, ex vivo stimulation and expansion of immune cells (such as T lymphocytes or dendritic cells, for instance), injection of genetically- or chemically-modified cancer cells, administration of inactivated viruses and gene therapy using nucleic acids encoding particular antigens or cytokines. While these various approaches allow the generation of an immune response against certain types of antigens or pathogenic agents, there is still a need for better methods of eliciting, regulating or stimulating an immune response. In particular, there is a need for simple methods of generating efficient immune responses, such as efficient cellular and/or humoral immune responses, against a variety of antigens, such as tumor antigens, viral antigens or other antigens from pathogenic agents.

The present invention now provides such a novel, alternative and improved method of causing, regulating or stimulating an immune response in a subject. The methods of this invention are simple, efficient and applicable to various antigens (or epitopes). More particularly, the invention now proposes to use synthetic viral particles to produce, modify or regulate an immune response in a subject against a variety of antigens. The invention is based, generally, on a new concept of using synthetic viral particles as an adjuvant and/or vehicle to raise an immune response against selected antigen(s) or epitopes, in particular a cellular and/or a humoral immune response. The invention also discloses particular embodiments related to the particles, cells or methods, their preparation and uses, which allow the generation of improved immune responses against antigens.

A particular object of the present invention resides in an immunogenic composition comprising:

a synthetic viral particle, wherein the synthetic viral particle comprises an antigenic molecule.

Another object of this invention resides in a method of producing, stimulating or regulating an immune response in a subject, comprising administering to the subject a composition comprising (and/or producing) a synthetic viral particle, wherein the synthetic viral particle comprises an antigenic molecule.

A further object of this invention lies in an immunogenic composition comprising a cell producing a synthetic viral particle as defined above.

The invention also relates to immunogenic compositions comprising a plasmid or a combination of plasmids, wherein said plasmid or combination of plasmids produces a synthetic viral particle as defined above upon transfection in a cell.

Particular immunogenic compositions on this invention comprise a plurality of synthetic viral particles (or cells or plasmids) as defined above, more particularly a plurality of different synthetic viral particles comprising a different antigenic molecule.

Preferably, the immunogenic compositions further comprise a pharmaceutically acceptable vehicle.

The invention also relates to methods of preparing the above synthetic viral particles, cells, or plasmids, as well as to methods of preparing the above immunogenic compositions.

The invention also resides in pharmaceutical compositions, medicaments and vaccines using or comprising the above compositions, either alone or in combination with additional active principles, adjuvants or carriers.

All the above embodiments will be described in further detail below, where the terms used have the general meaning known in the art, optionally supplemented with more specific or additional meanings, as indicated below:

Within the context of the present invention, the term "immunogenic" designates a product, composition or method that elicits, causes, stimulates or regulates an immune response or reaction. The immunogenic composition is thus any composition that modifies the activity of an immune system in a subject or in vitro. This includes protective immune responses, neutralizing immune responses, modification in antibody levels, modification in immune cell levels, etc.

The term "synthetic" designates non-naturally occurring material, produced by genetic engineering, synthesis, computerization, library screening, etc. in vitro, ex vivo or in vivo. Synthetic also includes artificial material, representing all or part of naturally-occurring material, optionally comprising modified structure(s) or moiety(ies). As an example, an artificial envelope may be produced that reproduces or mimics the structure or properties of an envelope, with particular properties (targeting, infectious power, fusogenicity, etc.).

"Gene" means any coding nucleic acid molecule. The term "gene" includes not only genomic DNA, but also cDNA, synthetic DNA, RNA, etc.

"Protein" This term is used interchangeably with "polypeptide" and designate any molecule comprising an amino acid or an amino acid chain, optionally modified, glycosylated, etc.

The term "antigen" (or antigenic molecule) designates any molecule such as a protein, polypeptide, peptide, lipid, nucleic acid, polysaccharide, epitope, etc. against which an immune response is sought, or a nucleic acid encoding the same. The antigen may cause direct immunogenicity, or be capable of indirect immunogenicity, by programming a cell to produce a molecule that elicits, causes or stimulates an immune response.

The expression "synthetic viral particles" designates non-naturally occurring viral particles produced as indicated above, typically by genetic engineering or synthesis, in vitro, ex vivo or in vivo. The synthetic viral particles may be of various origins and exhibit various particular features, as will be described below. In particular, although the following description is directed more specifically at synthetic retroviral particles, it should be understood that the teaching of the present invention can be transposed to other types of viruses, in particular AAV, adenoviruses, VSV, herpes viruses, and the like. Preferred viral particles according to this invention are synthetic retroviral particles comprising (or encoding) at least one synthetic component, preferably at least one synthetic envelope or gag protein. More preferably, synthetic retroviral particles of this invention may be (i) devoid of envelope, in particular devoid of an infectious wild-type retroviral envelope, or (ii) contain an envelope, in particular (a) a non-infectious envelope, (b) an infectious envelope, (c) a pH-dependent or pH-independent envelope (that fuses at low or neutral pH, respectively) and/or (d) a modified envelope The invention thus relates, generally, to compositions and methods of producing an immune response using synthetic viral particles, preferably synthetic retroviral particles. Generally, the synthetic viral particles comprise a proteic core comprising synthetic (modified) viral (structural) proteins, optionally combined with non-viral proteins. Also, as will be discussed, the synthetic viral particles may contain a nucleic acid molecule or genome. The invention indeed proposes to use particulate bodies comprising one or several identical or different synthetic viral protein(s) or polypeptide(s), typically one or several identical or different synthetic viral (structural) proteins, optionally (modified) viral proteins, to mediate an immune response. Such particles are efficient, simple, easier to manipulate than cells, etc. The immunogenic compositions of this invention may also include one or several identical or different synthetic viral protein(s) or polypeptide(s) from viruses of different origins or types, such as from retroviruses, adenoviruses, AAV, VSV and/or herpes viruses.

A particular embodiment of this invention resides in a synthetic viral particle as described above, wherein said viral particle is derived from vesicular stomatitis virus (VSV), typically from VSV-G. As will be described below, the particle may comprise various antigens, such as viral antigens (including HIV antigens) or tumor antigens, and may comprise a VSV-G envelope or a derivative thereof.

An other particular embodiment of this invention is a composition comprising a plasmid (or a combination of plasmids which, together) comprises the genes encoding a VSV particle comprising an antigen. Such a composition is suitable to produce, directly in vivo upon injection thereof, an immunogenic particle.

As indicated above, although not limited to a particular type of virus, the invention will now be described in more details with regard to synthetic retroviruses.

Typically, a simple retroviral particle comprises various structural proteins, such as a retroviral envelope protein, retroviral core proteins synthesised from the gag gene, and enzymes such as reverse transcriptase, proteases or integrase synthesized from the pol gene.

The synthetic retroviral particles to be used in the present invention are characterized by the particular structure, nature and/or composition of their proteic envelope (or core proteins, or enzyme), as well as by their nucleic acid content.

The synthetic retroviral particles may be produced, at least partially, from a large variety of retrovirus types and serotypes. In this regard, the particles may be prepared from onco-retroviruses, lentiviruses or spumaviruses. Onco-retroviruses have been used in the art for gene delivery purposes. They can be manipulated easily. Specific examples of onco-retroviruses include MoMLV (Moloney Murine Leukemia Virus) ALV, BLV, MMTV or RSV for instance. Lentiviruses represent another class of retroviruses, from which gene-delivery vectors have already been produced. Their genomic organization has been characterized and can be manipulated to target particular cell populations, notably quiescent cells. Specific examples of lentiviruses include HIV, SIV or EIAV, CAEV, for instance. Spumaviruses may also be used to produce synthetic retroviral particles according to the present invention. Their biology has been studied and importantly they are non-pathogenic in human beings. Examples of spumaviruses include HSRV2.

The Envelope Protein

In a particular embodiment, the synthetic retroviral particles comprise particular synthetic envelope proteins, to modulate their tropism and immunogenicity. In this respect, according to variants of this invention, the synthetic retroviral particles may be (i) devoid of envelope, in particular devoid of an infectious wild-type retroviral envelope, or (ii) contain an envelope, in particular (a) a non-infectious envelope, (b) an infectious envelope, (c) a pH-dependent or pH-independent envelope (that fuses at low or neutral pH, respectively) and/or (d) a modified envelope.

Particular envelopes that are suitable for use in the present invention are, for instance, the envelope of the following viruses: 4070A (Ott et al., J. Virol. Vol. 64 (1990) p 757-766), RD114, 10A1, VSV, LCMV, VIH, rabies virus or GALV (Delassus S. et al., Virology 173 (1989) 205-213, or derivatives thereof. The envelope may also be of cellular origin, such as a membrane protein allowing targeting of the retrovirus to a selected ligand, such as a CD4 receptor for instance. The envelope protein may also be fully synthetic, designed to target a specific receptor or structure or to mimic a specific antigen.

Specific tropism to professional Antigen-presenting cell—such as dendritic cells—may be used for efficient antigen presentation and inducing strong immune response.

Preferably, the envelope is (derived from) a retroviral envelope having tropism for mammalian cells, more preferably human cells, in particular an amphotropic or retargeted envelope. GALV, 4070A or 10A1, LCMV and VSV represent preferred embodiment for the construction of synthetic retroviral particles of the present invention.

As indicated, in a particular embodiment, the synthetic retroviral particle is devoid of an envelope protein, more particularly of a wild-type, infectious envelope. Immunogenic compositions comprising such non-infectious synthetic retroviral particles represent a particular and advantageous aspect of this invention. Indeed, such non-infectious synthetic retroviral particles are essentially unable to infect target cells, as would do most retroviral particles used so far in the art. However, such synthetic retroviral particles would still retain the ability to mediate an immune response, through other processing and presentation mechanisms, using for instance direct and passive membrane fusion, phagocytosis by antigen-presenting cells such as dendritic cells which capture particulate bodies, etc. Applicants believe that the use of such synthetic retroviral particles has never been disclosed or suggested in the art and provides a novel and efficient method of producing an immune response in a subject.

Such synthetic retroviral particles would thus essentially comprise gag proteins, an antigenic molecule and, optionally, non-infectious envelope proteins or polypeptides.

In this respect, according to another embodiment of the present invention, the synthetic retroviral particle comprises a non-infectious envelope. The non-infectious envelope does not allow the synthetic retroviral particles to infect target cells using conventional retrovirus infection pathways. However, the non-infectious envelope protein may provide for various functions on the synthetic retroviral particles. In particular, the non-infectious envelope proteins allow the anchoring of various molecules to the synthetic retroviral particles, including an antigenic molecule, a targeting moiety (such as a single chain antibody) (for example to target the particle to specific cell types such as dendritic cells), a tag, a purification agent, etc.

In a preferred embodiment, the non-infectious envelope protein comprises at least a portion of a retroviral envelope that is incorporated into the synthetic retroviral particles. In a more preferred embodiment, the non-infectious envelope protein comprises at least a functional portion of a retroviral envelope transmembrane domain.

According to an other variant of this invention, the synthetic retroviral particle comprises a pH-independent fusogenic envelope. These envelopes create synthetic particles with particular cell entry mechanisms. Indeed, such particles are able to enter directly into cells without the need to be routed to endosomes. Examples of such fusogenic envelopes include, for instance, VSV-G or influenza HA1.

In still another embodiment of this invention, the synthetic retroviral particle comprises a modified envelope. In a particular variant, the modified envelope is a synthetic (chimeric) envelope comprising at least a portion of the trans-membrane domain of a retroviral envelope fused to a foreign molecule. The foreign molecule may be an antigenic molecule, a targeting moiety such as a single chain antibody, a tag, a purification agent, etc. According to particular embodiments, the synthetic envelope comprises a purification agent, i.e., a non-natural portion that can be used to purify the particle through affinity interactions. In a specific embodiment, the purification agent is a ligand or an antigen and the particles are isolated, separated or purified using a corresponding receptor or antibody, preferably immobilized on a support such as beads, a column, a filter, etc.

In an other embodiment, the synthetic envelope is functionalised, thereby allowing the binding, to the synthetic envelope, through covalent or non-covalent interaction, of any selected molecule of interest. The functionalised envelope may, for instance, comprise a linker wherein the linker allows (specific) binding of any selected molecule of interest. As an example, the envelope may comprise an avidine or biotine moiety, allowing specific binding thereto of a molecule. The bound molecule may be proteic or non proteic, such as an epitope, antigen or a artificial molecule mimicking said antigen or epitope, for instance. This invention resides in any particulate body or immunogenic composition comprising a functionalised envelope as described above.

It should be understood that the above variants can be operated individually, or in various combinations (see FIG. 5). In this regard, the invention now proposes to use synthetic retroviral particles comprising at least two different envelope proteins, to further improve the properties of the immunogenic compositions of this invention.

In this regard, in a particular embodiment, the invention relates to an immunogenic composition comprising (i) a synthetic retroviral particle, wherein the synthetic retroviral particle comprises at least two different envelope proteins and an antigenic molecule, and (ii) a pharmaceutically acceptable vehicle.

According to particular variants of the present invention, the two different envelope proteins may be as follows:
an infectious envelope and a non-infectious envelope,
a modified envelope and a wild-type envelope,
a modified (chimeric) envelope carrying an antigen and an infectious envelope
a modified (chimeric) envelope carrying a tag and an infectious envelope
a modified (chimeric) envelope carrying a targeting motif such as a single chain antibody and an infectious envelope
a modified (chimeric) envelope carrying a targeting motif such as a single chain antibody and a modified (chimeric) envelope carrying an antigen
a synthetic or artificial envelope designed to mimic a selected antigen
a synthetic or artificial envelope designed to target a receptor, or
a synthetic, functionalized envelope (e.g., comprising a linker).

The nature, structure and activity of the envelope protein determines the activity of the synthetic particles.

Localization of the recombinant particle within the host cell influences the antigen processing pathway, the nature of the antigen and the relative contribution of effector immune cells.

Specific interaction with cytoskeletal of target cell can change the pathway of particle transit and changes its processing. Translocation of retroviral particles into phagosome permits loading of different presentation molecules: MHC-II, MHC-I and CD1. Respectively, CD4 CD8 and NK T cells would be primed. Translocation of retroviral particles from the cytoplasm into endoplasmic reticulum allows loading of MHC-I molecules and so priming cytotoxic T lymphocytes. The examples show that the synthetic particles and constructs of this invention can be effectively processed and presented, resulting in a stimulation of a specific CTL response.

Inducing overexpression of class-I and class-II peptide complexes permits to increase antigen sensitization. Up-regulation of peptide transport activity in presenting cells leads to efficient antigen presentation and immune response.

The synthetic retroviral particles may contain several additional proteins or molecules, such as (modified) gag retroviral proteins, retroviral proteins such as NEF, vpr, etc., as well as antigenic molecule(s). In a particular embodiment, the synthetic retroviral particles as described above comprise a retroviral gag protein, even more preferably a modified retroviral gag protein.

Gag Protein

In a particular embodiment, the synthetic retroviral particles as described above comprise a retroviral gag protein, even more preferably a modified retroviral gag protein. In a specific example, the gag protein is a chimeric protein comprising an antigenic moiety. Indeed, as described in the present application, the inventors have now shown that antigenic molecules can be produced as a fusion with gag protein, without affecting the synthesis efficiency.

Particle assembly is driven by Gag polyprotein precursors. Incorporation of the Gag-Pol precursor is mediated by Gag sequences (FIG. 1A), suggesting that replacement of Pol by a different protein would result in a Gag-fusion protein that could also be incorporated into retroviral particles. Indeed, fusion of 3-galactosidase to the C-terminus of MLV or HIV-1 Gag proteins resulted in specific incorporation of the fusion protein in the virions, and the protein retained enzymatic activity (Jones et al., 1990; Wang et al., 1994b). Similar results were obtained when staphylococcal nuclease was fused to MLV Gag (Natsoulis et al., 1995) and cytochrome c fused to the RSV Gag (Weldon et al., 1990). For the MLV Gag-fusion protein, the presence of wild-type Gag was required for the formation of viral particles, provided either by co-expression of the Gag precursor (Jones et al., 1990) or by superinfection with wild-type MLV (Natsoulis et al., 1995). This implies that the total amount of the Gag-fusion protein incorporated into the particle will be lower than the total amount of Gag protein found in wild-type virus particles. For example, even with the most efficient chimeras (Jones et al., 1990), the number of β-galactosidase molecules associated with virions was estimated to be approximately 70, compared to 2000 molecules of Gag. For this strategy to be applied to vectors, it is necessary to incorporate the maximum amount of the foreign protein possible and since Gag is the most abundant component of the virion it is desirable to aim in incorporation of the protein in equimolar amounts to Gag. An alternative strategy would be to insert the foreign protein within the Gag precursor. The problem with this approach is that most of the MLV Gag protein is extremely sensitive to insertions or deletions (Hansen et al., 1990; Lobel and Goff, 1984; Schwartzberg et al., 1984). Two regions were identified that could be deleted without affecting particle assembly, although the resulting particles were not infectious. The first region was located around the MA-pp12 junction (Crawford and Goff, 1984) and the second in the N-terminus of NC (Schwartzberg et al., 1984). Insertions of 4 amino acids within these regions could also be tolerated, again without affecting assembly but affecting infectivity (Hansen et al., 1990). Nevertheless insertion of larger polypeptides might have a more dramatic effect.

Certain lentiviruses encode an additional protein, named p6, at the carboxy-terminal end of the Gag protein precursor (FIG. 1B). We have inserted a fragment corresponding HIV-1 p6 in MLV Gag precursor and before the pol gene. In order to produce infectious particles, we inserted the p6 protein in the Gag-Pol precursor containing an active protease and reconstituted the MLV protease cleavage sites and Gag-Pol junction site that allows the balanced expression between Gag and Gag-Pol precursors. It should be understood that the presence of such site is optional and that non-infectious particles may be produced and used within the context of the present invention.

The first consideration was where in the Gag-Pol precursor p6 would be inserted. With the hope to obtain expression to levels equivalent to the unmodified Gag proteins, we chose to insert p6 at the C-terminal end MLV Gag, after the nucleocapsid protein to minimize interference with the overall structure and function of the Gag precursor. Furthermore, in a specific embodiment, the protease cleavage sites around p6 was reconstituted.

Retroviral proteases are highly specific for their own native precursor molecules (Skalka, 1989). Generally, the target sites consist of hydrophobic residues and the structure around the site appears to be important for substrate specificity. Specificity is influenced by 4 amino acids N-terminal to the cleavage site referred to as P4, P3, P2 and P1, and 4 amino acids immediately C-terminal to the site, P1', P2', P3' and P4'. Cleavage occurs between P1 and P1'. Synthetic peptides that can act as substrates to viral proteases have been synthesized and demonstrate that it is possible to reconstitute the protease cleavage sites (reviewed in Krafft, 1994).

The cleavage site between NC and PR was reconstituted at both ends of p6. The sequence surrounding this cleavage site is:

| NC | | | | PR | | | |
|---|---|---|---|---|---|---|---|
| P4 | P3 | P2 | P1 | P1' | P2' | P3' | P4' |
| Thr | Ser | Leu | Leu | Thr | Leu | Asp | Asp |
| (ACC | TCC | CTC | CTG | ACC | CTA | GAT | GAC) |

Figure 2:
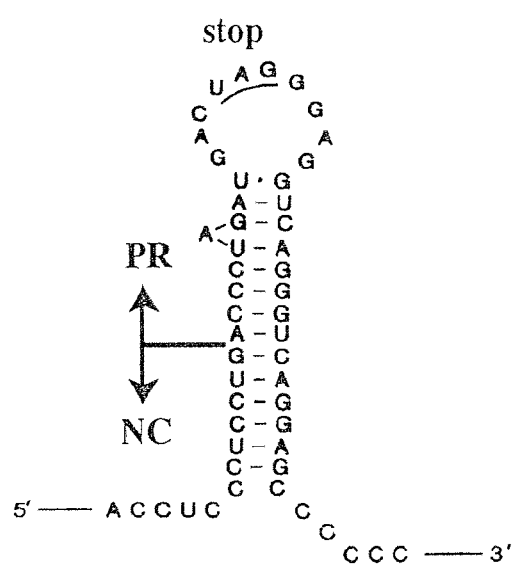

For the junction between NC and p6 the 4 C-terminal amino acids of NC were retained and the 4 N-terminal amino acids of PR were fused to p6. The C-terminus of p6 was more problematic due to the termination codon located at the Gag-Pol junction. Pol proteins are expressed only when this codon is suppressed. The nucleotides around it form an secondary structure that participates in both the function of the termination codon as well as its suppression (Felsenstein and Goff, 1992; Feng et al., 1992; Jones et al., 1989; Wills et al., 1991). Several models representing the secondary structure formed have been proposed, a simplified version of which is shown as a stem loop in FIG. 2. The 5' part of the sequence predicted to participate in this structure involves the 3' terminal 6 nucleotides of gag and the 5' end of pol and. This nucleotide sequence corresponds to the junction between NC and PR proteins, specifically residues P4 to P4'. Nucleotides corresponding to P4 through to P4' form the 5' part of the stem loop with the termination codon located immediately after the P4' amino acid codon.

Since the Gag-p6 chimera p6 replaces NC at the C-terminus of Gag, it was important that the DNA sequence of the NC-PR junction participating in the stem loop was reconstituted. Thus, the 3' 12 nucleotides of the NC DNA (containing only a single base pair change to create a restriction site in the sequence not involved in the 5' stem formation) were introduced in the 3' end of the p6 DNA. The 5' end of the PR DNA sequence was left intact, hence reconstituting the NC-PR cleavage site.

The p6 protein is located at the extreme C-terminus of the Gag polyprotein precursor of HIV and SIV viruses and varies both in length, from 52 to 64 amino acids, and amino acid sequence among the different virus groups (Barrie et al., 1996). For the generation of the MLV Gag-p6 chimera residues 5-48 of p6 from the pNL4.3, a recombinant infectious HIV-1 proviral clone, were used. The 4 N-terminal amino acids were replaced by the first 4 N-terminal amino acids of the MLV PR and the last 4 C-terminal amino acids were replaced by those of MLV NC to reconstitute the MLV protease cleavage sites as described above.

The results presented In this application show that particles thus produced contain high amounts of antigenic molecule, are infectious (provided they contain an functional env protein), and can be produced at high titers.

The present application thus relates to immunogenic synthetic particles comprising a chimeric gag protein, said chimeric gag protein comprising an antigenic moiety (molecule) and, optionally, further comprising an envelope protein as described above.

The synthetic particles of this invention may thus comprise an envelope as described above and/or a gag protein as described above and an antigen. As indicated, these various embodiments may be used in all possible combinations.

The Antigen

The synthetic (retroviral) particles of the present invention comprise an antigenic molecule. The antigenic molecule may be a tumor antigen, a bacterial antigen, a pathogenic antigen, a proteic antigen, a viral antigen, etc. Typical examples and preferred uses of the instant invention are for generating an immune response against viral antigens or tumor antigens. Specific examples of such antigens include oncospermatogonal antigens (MAGE-1, . . . ), oncofetal antigens (MAGE-3, P1A, CEA, etc.), differentiation antigens (17-1A, PSA, Tyrosinase, Lewis, HER-2/neu, GD2/GD3 ganglioside, etc.), clonal antigens (Immunoglobulin idiotype, etc.) and mutant cellular gene products such as mutant ribosomal protein (Mut L9, etc.), mutant cyclin (Mut cdk4, etc.), mutant oncogene (Mut.p21s, etc.), mutant suppressor gene (Mut.p53s, etc.), mutant chimeric fusion protein (BCR-ABL, etc.), etc. Typical examples of such viral antigens include gp120, gp160, gag epitopes, V3-loop peptide, etc., derived from HIV; pp65, IE1, gB, pp150, PP28, etc. from cytomegalovirus; gp85, gp340, gp350, p-2B, etc. from EBV.

The antigen may be exposed at the surface of the synthetic retroviral particle, included in the particle or encoded by the particle (when the particle further comprises a nucleic acid molecule, as described below).

In a preferred embodiment, the antigen is a polypeptide or peptide exposed at the surface of the particle. In this regard, the antigen may be exposed through binding to various structures, such as to an envelope protein or a portion thereof, a gag molecule or a portion thereof, a synthetic linker, or through chemical or enzymatic reaction, including antibody, VPR protein (which binds to gag), etc.

It is clear from the above description that the antigen may be constituted by the particle itself, when said particle is from a virus or comprises parts of a virus against which immunisation is sought. For instance, where the particle derives from a HIV retrovirus, it can constitute the antigen. When the particle derives from a MLV or VSV virus, it comprises further antigenic motifs that are typically heterologous with respect to the virus.

Exposure of the antigen at the surface of the particle is one of the preferred embodiment of this invention.

In this regard, particular compositions of the instant invention are:

An immunogenic composition comprising:
a synthetic retroviral particle, wherein the synthetic retroviral particle is (i) devoid of a retroviral genome, (ii) devoid of a wild-type, infectious envelope and (iii) comprises, exposed on the surface thereof, an antigenic molecule;

An immunogenic composition comprising:
a synthetic retroviral particle, wherein the synthetic retroviral particle is (i) devoid of a retroviral genome, (ii) comprises a fusogenic envelope and (iii) comprises, exposed on the surface thereof, an antigenic molecule.

As indicated above, preferred antigens are viral antigens, specifically HIV antigens. The invention thus relates to a synthetic viral particle that comprises one or several HIV antigens (or epitopes), as described above. The particle preferably comprises a non-replicating genome or is devoid of a genome. The particle typically comprises a viral core structure made of retroviral or VSV-G proteins. Typically, the viral particle comprises a gag and pol protein from a retroviral or VSV virus and an envelope protein from a HIV virus. Alternatively, the viral particle comprises a gag and pol protein from a retroviral or VSV virus, an envelope protein from a VSV virus and an antigenic molecule (typically from HIV) exposed at the surface of the particle, for instance by genetic or chemical fusion with the VSV envelope protein or a portion thereof.

In a more specific embodiment, the antigen is exposed through binding to an envelope protein or to a gag protein, as discussed above. In these embodiments, the antigen preferably consists of a synthetic peptide or polypeptide containing between 3 and 60 amino acids, even more preferably between 3 and 30 amino acids. In a preferred example, the synthetic retroviral particle comprises a synthetic (chimeric) gag protein, wherein the gag protein comprises an antigenic molecule. As disclosed in the examples, the antigenic molecule is preferably fused to the C-terminal end of the gag protein. In this regard, an object of the present invention resides in a method of causing or stimulating an immune response in a subject, comprising administering to the subject an effective amount of a composition comprising a synthetic gag protein, wherein the synthetic gag protein comprises an antigenic molecule. Even more preferably, the synthetic gag protein is a chimeric protein comprising all or part of a retroviral gag protein covalently linked to an antigenic molecule. Even more preferably, the composition is a viral particle comprising said synthetic gag molecule.

Alternatively, the antigen when expressed on the surface of the particle can be a large molecule that can be recognized by antibodies. Likewise, they can be efficiently captured by specific B cells; after processing of the viral proteins, they will efficiently present antigenic epitopes to T cells. Likewise, the synthetic retroviral particles can activate the two arms of the immune response, humoral and cellular.

In this regard, the invention now describes that efficient antigen expression is achieved when an antigen is produced as a fusion molecule with gag protein. As described in the examples, the fusion may further include protease cleavage site, to ensure release of the antigen upon expression of the fusion (chimeric) molecule. Alternatively, the fusion may lack such protease cleavage site.

In an other particular embodiment, a composition of this invention comprises a first synthetic retroviral particle, wherein the first particle comprises a chimeric gag protein, wherein the gag protein comprises an antigenic molecule and a second synthetic retroviral particle, wherein the second particle comprises a chimeric env protein, wherein the env protein comprises an antigenic molecule.

Indeed, the invention now proposes to use combinations of antigen presentation strategies using synthetic retroviral particles to maximize the immunogenicity. In this regard, it is believed that the type of antigen presentation (e.g., exposure at the surface, fusion with envelope or gag, inclusion within the particle, various HLA conformation), nature of particle (infectious or non-infectious, targeted or not) and presence of additional immunomodulators encoded by the genome, significantly determines the processing pathway and type of immune response generated against the antigen.

Generally, it is believed that where the antigen is exposed or contained in the particle, a cellular class II immune response and mechanism will be initiated. Alternatively, where the antigen is encoded by the particle, a humoral class I immune response is expected to be initiated. The present invention thus allows to improve the immune reaction of a host organism, by combining several presentation and processing pathways of an antigen.

In this regard, further objects of the present invention relate to:

An immunogenic composition comprising a plurality of synthetic viral particles as described above, An immunogenic composition comprises a plurality of (e.g., at least 2, preferably at least 3, even more preferably at least 4) different synthetic viral particles as described above, wherein said synthetic viral particles comprise a different antigenic molecule.

An immunogenic composition comprising a plurality of (e.g., at least 2, preferably at least 3, even more preferably at least 4) different synthetic viral particles, wherein said synthetic viral particles comprise a common antigenic molecule to be presented by different HLA molecules. It is known that epitopes are processed and presented differently across various subjects, based on their HLA molecules. The present invention now proposes compositions comprising combinations of a same epitope in different conformations, to provide an immune response in various subjects with different HLA serotypes. Typically, the antigen is a peptide and the plurality of different synthetic retroviral particles comprise the epitope with flanking sequences varying in length.

Antibody affinity of peptide can be modulated by the flanking sequences, in correlation with their capacity to maintain the antigenically reactive structure. Synthetic peptides may be prepare by grafting N- and/or C-terminal sequences to increase both in affinity and in inhibitory potency.

Residues that flank the epitope may influence its proteolytic process, modulating its presentation. Both N- and C-terminal flanks of the epitope are determinant for cleavage and may contribute to the phenomenon of immunodominance.

Peptides can be prepared with extensions composed of native and/or non-native sequences to increase affinity to MHC molecules. It is possible to construct synthetic CD8+ and/or CD4+ T-cell stimulatory peptides of high potency from a non-stimulatory epitope.

The length of the flanking regions adjacent to epitope can be modulated to modified the cleavage production by proteasomes.

The above composition may comprise, preferably, synthetic retroviral particles, or a mixture of viral particles of different types.

The synthetic particles of this invention may thus comprise an envelope as described above and/or a gag protein as described above, an antigen, and/or a nucleic acid molecule as described below. As indicated, these various embodiments may be used in all possible combinations.

The Nucleic Acid Molecule or Genome

As indicated above, the synthetic viral particles of the present invention as described above may also be further characterized by the presence, absence and/or structure of a nucleic acid molecule or genome. In this respect, various embodiments can be used in the instant invention. Generally, the synthetic retroviral particles may (i) be devoid of a retroviral nucleic acid genome or (ii) contain a (synthetic) retroviral nucleic acid genome, which can be (a) replication defective or (b) replication competent.

In this regard, in a particular variant, the synthetic retroviral particles are devoid of genome, more specifically of a retroviral genome. In this embodiment, "empty" synthetic retroviral particles are used. This variant is particularly advantageous in terms of safety, since no viral DNA replication or dissemination may occur upon administration.

In another variant, the synthetic retroviral particles, or at least a portion thereof, contain a synthetic or natural retroviral nucleic acid genome. The presence of a genome may offer the following alternatives. It may allow the production of desired molecules, such as the antigenic molecule or immunomodulatory molecules, for instance. It may also be possible to produce multiple cytokines, changing the environment and then control the differentiation of immune cells. For example, expression of IL-12 and/or IFNg cytokines induces Th cells capable of effective cell-mediated immunity responses (Th1 cells). Alternatively, IL-4 and/or IL-10 secretion furthers the development of Th2 cells, essential for the induction of the humoral immune responses and the suppression of cell-mediated immunity.

It is thus possible to produce chemokines—chemoattractant cytokines—to induce the directional migration of immune cells and enhance their activation. With specific chemokines, CXC chemokine (IL8, GRO, NAP-2, GCP-2, PF-4, IP-100, MIG, . . . ) and/or C-C chemokine (MCP-1 to -5, MIP-1, RANTES, . . . ), it is possible to promote humoral and cell-mediated immune reactions; regulate cell adhesion, angiogenesis, leukocyte trafficking, and homing; and contribute to lymphopoiesis and hematopoiesis (baggiolini et al, 1997; Taub 1996).

It may also allow the expansion of the particles in vivo, and thus increase the immunogenic activity of the composition. It may also facilitate the follow up or control over the therapeutic effect, by expressing a conditionally-toxic molecule, for instance.

In this regard, the retroviral genome may be a replication-defective genome or a replication-competent genome.

Within the context of the present invention, the term "replicative" means that the genome contains the genetic elements allowing replication thereof in the absence of any trans-complementing function. Synthetic retroviral particles containing replicating genomes are also termed replication-competent particles. In contrast, a replication-defective genome is a genome that is not capable of replication in the absence of trans-complementing functions, and thus lacks at least one functional retroviral gene necessary for replication.

It is known that the genomic organization of retroviruses comprises essentially the following elements:
- a LTR ("Long Terminal Repeat") region, located at each end of the genome, Each LTR region is composed essentially of three functional regions termed U3, R and U5,
- a packaging sequence ("Psi"), involved in the packaging of the proviral genome in the viral particle,
- three coding regions, designated gag, pol and env, coding the core proteins (gag), the enzymes (reverse transcriptase, protease, integrase) and the envelope glycoprotein (env).

In the case of lentiviruses, their genome further comprises additional coding or regulatory sequences, such as vif, vpr, vpu, vpx, rev, tat, and nef.

In a particular embodiment, the composition comprises a synthetic retroviral particle comprising a replication-defective retroviral genome, wherein the retroviral genome lacks at least one functional gene selected from gag, pol and env.

The (synthetic) gene may be either mutated, deleted (entirely or partially) or contain inserted sequences that prevent functional expression or activity. Preferably, the replication-defective retroviral genome comprises a deleted gag and/or pol and/or env gene.

A replicative retroviral genome according to the present invention is more preferably a retroviral genome (e.g., a nucleic acid) comprising at least functional gag, pol and env genes. More specifically, the replicating retroviral genome comprises (i) wild type or modified but still functional gag, pol and env genes, (ii) a retroviral packaging sequence and (iii) two retroviral LTR sequences. The replicative vector can be made from wild type genome or from attenuated genome, ie genome modified to limit or slow the replication of these viruses A replicating lentivirus-type retroviral construct of the instant invention would thus preferably comprise elements (i)-(iii) listed above as well as (iv) functional vif, vpr, vpu, vpx, rev, tat and nef sequences, or only a part thereof necessary for replication of the viral genome.

Furthermore, the retroviral nucleic acid genome may further contain foreign nucleic acid(s), such as genes, promoters, regulation sequences, etc, that facilitate or improve the immunogenic activity of the composition. These can be modified LTR engineered to be cell specific or regulatable.

In a particular embodiment, the retroviral genome comprises a nucleic acid molecule encoding a polypeptide of interest, more particularly a foreign (or (heterologous) polynucleotide, i.e., a polynucleotide not naturally present in a wild-type retroviral genome.

Within the context of the present invention, the expression "polynucleotide" designates any nucleic acid molecule whose delivery to a cell, culture, tissue, organ or organism is desired. In a preferred embodiment, the polynucleotide encodes a polypeptide selected from an antigen, an immunomodulator or a palliative.

In a particular embodiment, the synthetic retroviral particle comprises a nucleic acid genome encoding an antigen. Indeed, in particular embodiments, the antigen is encoded by the retroviral genome. In this embodiment, the antigen may be encoded by the foreign nucleic acid (the polynucleotide) or as a fusion molecule, for instance with gag or env.

In a preferred variant, a composition of this invention comprises a synthetic retroviral particle, wherein the particle contains a retroviral genome encoding an antigen fused to a gag polypeptide.

In an other preferred embodiment, a composition of this invention comprises a first synthetic retroviral particle, wherein the first particle contains a retroviral genome encoding an antigen fused to a gag polypeptide and a second synthetic retroviral particle, wherein the second particle contains a retroviral genome encoding an antigen fused to an env polypeptide.

The polynucleotide may also encode an immunomodulator, i.e., any protein that regulates an immune response. The immunomodulator may stimulate the immune response, inhibit particular immune cells, etc. Typical examples of immunomodulators include cytokines (e.g., interleukins (IL-2, IL12, IL4, IL13, IL15 etc.); interferons, TNF, F1T3-L etc.), hematopoietic growth factors (G-CSF, GM-CSF, CSF, etc), costimulatory molecules (B7, CD40 or CD40L), and the like. Other molecules of interest may be anti-angiogenic factors, immunostimulant or immunosuppressive cytokines, chemokines, etc.

In this respect, particular embodiments of the present invention are immunogenic compositions comprising:
  a synthetic retroviral particle, wherein the synthetic retroviral particle comprises (i) a retroviral genome encoding an immunomodulator and (ii) an antigenic molecule;
  or,
  a synthetic retroviral particle, wherein the synthetic retroviral particle comprises (i) a retroviral genome encoding an immunomodulator, (ii) an antigenic molecule, (iii) is devoid of a wild-type, infectious, retroviral envelope;
  or,
  a synthetic retroviral particle, wherein the synthetic retroviral particle comprises (i) at least two different envelope proteins, (i) a retroviral genome encoding an immunomodulator or antigenic molecule, and (iii) an antigenic molecule.

The synthetic particles may be prepared according to general methodologies known to the skilled person. In particular, the various nucleic acid molecules, genomes or reconstituted vectors or plasmids may be prepared using the sequence of known viruses. Such sequences are available from banks, and the material may be obtained from various collections, published plasmids, etc. These elements can be isolated and manipulated following techniques well known to the skilled artisan, or isolated from plasmids available in the art. The various synthetic or artificial sequences may also be produced from computer analysis or through (high throughput) screening of libraries.

The synthetic retroviral particles may be prepared according to techniques known in the art. In particular, they may be produced using conventional packaging cells or through transient transfection. Suitable packaging cells include any cell permissive to retrovirus infection, which can be cultivated in vitro, and is essentially devoid of any pathogenic property. Typical methods of producing retroviruses in vitro are disclosed for instance in WO89/07150, WO90/02806, U.S. Pat. No. 4,861,719, WO98/02529. Typically, the production comprises culturing a packaging cell expressing the gag and/or pol and/or env proteins, as described above, and collecting the produced particles. Where the particles comprise a retroviral nucleic acid genome, the packaging cells can be transformed with said nucleic acid molecule, and the particles are collected. The particles may be purified according to known techniques, such as centrifugation, gradients, chromatography, etc. The cell supernatant may be used directly, with no purification step.

In a preferred embodiment, the retroviral particles are produced in a packaging cell of mammalian origin, more preferably of murine or human origin. In a further preferred embodiment, the particles are produced in vitro using a packaging cell of human origin, with determined HLA type or glycosylation pattern, to further control immunogenicity of the particle. Such cells may be fibroblasts, retinocytes, hepatocytes, in particular in a mature, embryonic or immortalised status.

Where plasmids are used to produce the particle in vivo, production may be accomplished as described in WO95/22617, for instance.

Where replication-competent retroviral particles are being used, they may be prepared according to EP00401568.1.

All publications or citations are incorporated therein by reference.

An object of this invention also resides in a retroviral packaging cell, wherein the cell expresses at least two different envelope proteins. The packaging cell preferably derives from a mammalian cell, more preferably a murine or human cell. The cell should lack recognized pathogenic activity, and be cultivable under appropriate conditions. The cell generally comprises two constructs inserted in its genome that encode, respectively, each of the envelope proteins. The cell typically derives from a fibroblast, hepatic, epithelial, or muscular cell, or from a precursor or progenitor thereof, such as embryonic cells, typically from kidney, muscle, retina, etc.

Further immunogenic compositions of this invention comprise (i) a cell producing a synthetic retroviral particle as described above or (ii) a plasmid or a combination of plasmids, wherein said plasmid or combination of plasmids produces a synthetic viral particle as described above upon transfection in a cell. In this regard, a particular object of this invention is a composition comprising a plasmid, said plasmid comprising a gene encoding an envelope protein and/or a gag protein and/or a nucleic acid genome as described above. A preferred composition comprises a plasmid encoding an envelope protein and a gag protein and a nucleic acid genome as described above. An other preferred composition comprises a plasmid encoding an envelope protein and a gag protein as described above. In an other embodiment, the gag and/or pol and/or env proteins are encoded by separate plasmids. The plasmids may be derived from any known commercial plasmids, and may further comprise a marker gene and/or an origin of replication that allows manipulation in vitro.

Figure 3:
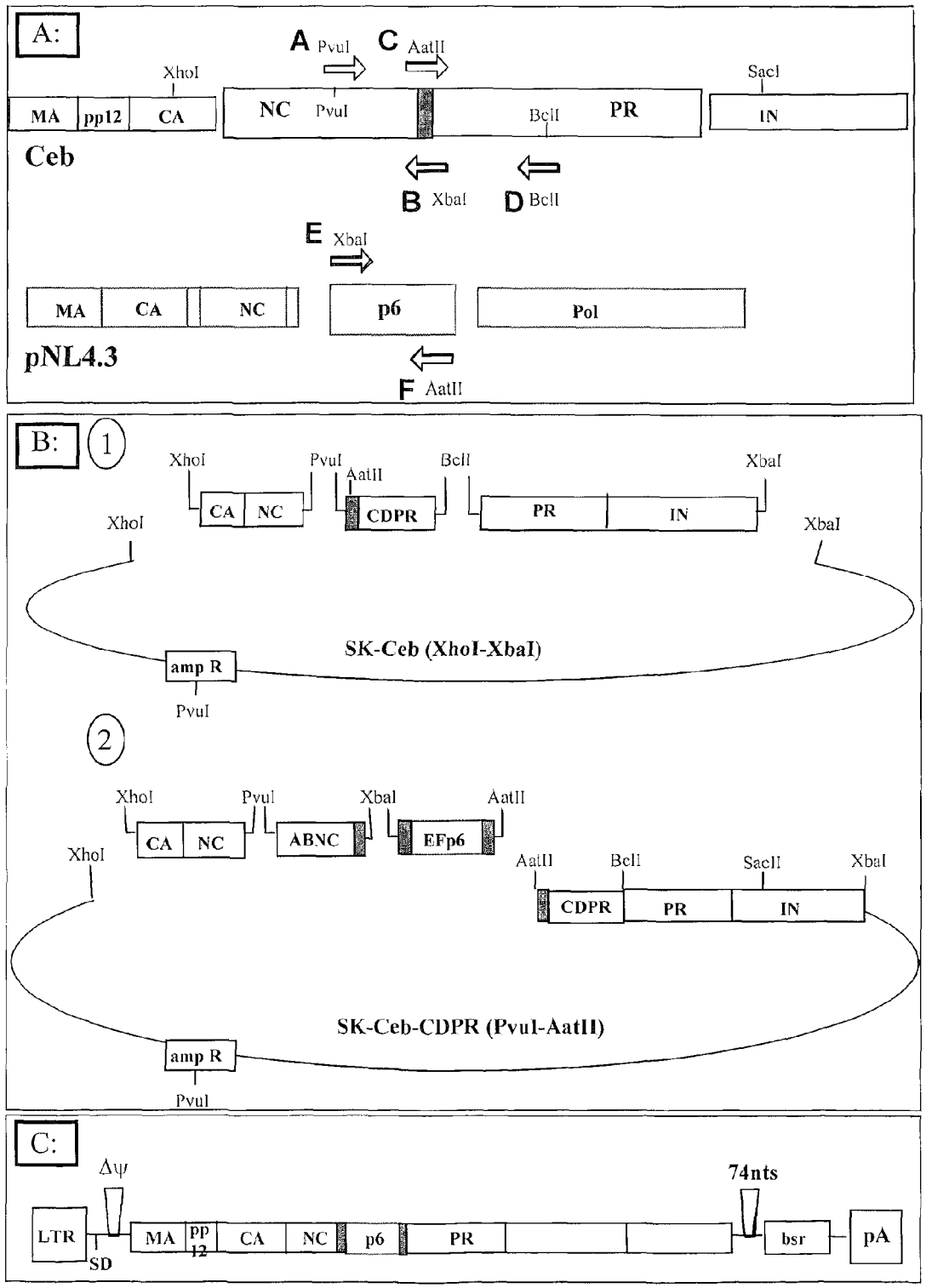

In a specific embodiment, the invention relates to a composition comprising one or several plasmids, which, alone or in combination, produces a synthetic VSV particle comprising an antigen. Although plasmids are much preferred, they may be replaced by other gene delivery systems, such as other viral systems, for instance. In a particular embodiment, the composition comprises a plasmid comprising a gene encoding a VSV envelope protein and/or a gene encoding a VSV core structural protein and/or a nucleic acid genome as described above, and an antigen. A preferred composition comprises one or several plasmids encoding, alone or in combination, a VSV envelope protein, VSV core structural proteins and an antigen, the antigen being expressed as a fusion molecule with all or part of the envelope protein. Such a composition allows, upon in vivo injection, the production of a VSV synthetic particle expressing an antigen. Because the VSV-G envelope is able to infect various cell types, particularly mucosal cells, this composition has a high immunogenic potential. It is particularly suited to express tumor or viral antigens, especially HIV antigens.

The compositions according to the present invention may comprise any pharmaceutically acceptable vehicle, such as saline solutions, buffer, isotonic solute, etc. Furthermore, the compositions may comprise additional adjuvants or immunogenic or biologically active agents. Generally, the compositions comprise an effective amount of the particles, such as between about $10^2$ and $10^9$, generally between $10^2$ and $10^6$, typically between $10^3$ and $10^5$ particles. The compositions may be administered by various routes known to the skilled artisan, which may be adjusted depending on the antigen, pathology, biological effect, plasmid or particle, etc. Examples of administration routes include parenteral injection, such as intravenous, sub-cutaneous, intra-dermic, intramuscular and intraperitoneal injections. When the composition comprises empty particles, it is typically administered in the circulatory system. When it comprises a particle comprising a genome or when it comprises a plasmid (or a combination of plasmids), it is typically administered in a tissue of the subject, typically in the muscle, although other administration protocols can be carried out.

The invention also relates to methods of causing or stimulating an immune response in a subject, particularly a CTL response, comprising administering a composition as described above to a subject in need thereof.

The invention also relates to the use of a composition as described above in the manufacture of a medicament suitable for causing or stimulating an immune response in a subject, particularly a CTL response, more preferably against a human immunodeficiency virus antigen.

Other aspects and advantages of this invention will be disclosed in the following examples, which are only illustrative and not limitative.

LEGEND TO THE FIGURES

FIG. 1: Genetic Organization of MLV (FIG. 1A) and HIV (FIG. 1B) viral genomes. Open rectangles indicate the open reading frame of the gene/genes marked. Horizontal lines between rectangles in HIV-1 schema indicate segments removed by splicing. Arrows point to translation products indicated by light grey rectangles. Only the translation products dealt with by this section are shown. (A) The X indicates the interaction between the Vpr protein and the p6 region of the HIV-1 Gag. (B) The stop codon of MLV Gag protein is indicated. Suppression of this codon leads to synthesis of the Gag-Pol precursors.

FIG. 2: Gag stop codon stem loop (SEQ ID NO: 7). Proposed RNA secondary structure around the gag-pol junction of Mo-MLV (from Jones et al., 1989). The sequences coding for NC and PR after protease cleavage are indicated. The Gag stop codon is underlined.

FIG. 3: Construction of the Ceb-p6 Chimera

FIG. 4: Expression of Gag-p6 chimeras and virion formation. Immunoblots lysates from cells expressing the Ceb constructs indicated (A) and of pellets of the viral supernatant from these cells (B). Results obtained from polyclonal series 2 are shown. Staining was performed using antibodies against the MLV capsid, p30, protein.

FIG. 5: Schematic representation of synthetic retroviral envelope (5A) and gag (5B) proteins, genome (5C) and particles or according to this invention.

FIG. 6: In vivo modulation of an immune response using synthetic retroviral particles.

FIG. 7: Stimulation of CTL using synthetic envelope particles of this invention.

EXAMPLES

A—Incorporation of Foreign Nucleic Acids or Proteins in Synthetic Retroviral Particles A1. Materials and Methods A1.1. Insertion of HIV-1 p6 into the MLV Gag-Pol Precursor.

The p6 coding sequence was inserted into the Ceb plasmid which expresses the Gag-Pol precursor and a blasticidine resistance marker using the MLV LTR (long terminal repeat) as promoter. This plasmid has been previously used to establish several stable packaging cell lines such as TELCeB6 and FLY using blasticidine selection (described in Cosset, 1995b). Briefly the plasmid consists of the LTR, the leader sequence deleted for the encapsidation signal ψ and the polyadenylation signal from the MLV strain FB29. The Gag-Pol coding sequence has been obtained from MoMLV. The bsr (blasticidine) resistance marker was inserted 74 nucleotides downstream of the pol stop codon. Although the level of Gag-Pol expression in stable populations of mammalian cells is very high, Ceb was constructed using the low copy number pBR322 plasmid. Thus, of the gag-pol sequence was transferred into a high copy number plasmid, bluescript SK, to facilitate the cloning procedure. A segment of the MLV Gag-Pol coding sequence, from the XhoI site in the beginning of gag (position 1668) to the XbaI site in the integrase coding sequence (position 5437), was excised and cloned into the XhoI-XbaI digested SK plasmid. This cloning intermediate was named SK-Ceb.

The cloning procedure consisted of insertion of several fragments at once since the number of unique sites in the Ceb sequence and backbone plasmid was limited (FIG. 3). The first step consisted of introducing the required enzyme restriction sites as well as the protease recognition DNA sequences using PCR with appropriately designed primers. The sequences targeted as well as the restriction sites introduced by each primer are shown in FIG. 3A.

The NC coding sequence was modified using 5' primer A and 3' primer B. Primer A hybridizes in the NC DNA at the PvuI site at position 2228 of Ceb. Primer B hybridizes to the DNA at the junction between NC and PR and introduces a XbaI restriction site at the sequence coding for the amino acids at positions P2' and P3' of the protease cleavage site. The 100 base pair PCR product was named ABNC.

The protease coding sequence was amplified using 5' primer C and 3' primer D. Primer C hybridizes to the DNA at the junction between NC and PR and introduces a PvuI site followed by an AatII site at the sequence encoding the amino acids at position P2 and P3 of the protease cleavage site. Primer D hybridizes in the PR DNA sequence at the BclI site located at position 2848 of Ceb. The 500 base pair fragment was named CDPR.

The p6 coding sequence was amplified using the 5' primer E and the 3' primer F. Primer E hybridizes to the 5' of p6 DNA (downstream from codon 5) and introduces 10 nucleotides coding for the amino acids at positions P2', P3' and P4' of the protease cleavage site and a XbaI restriction site. Primer F hybridizes to the 3' end of the p6 DNA (upstream from codon 48) adding 11 nucleotides coding for amino acids at positions P1, P2 and P3 of the protease cleavage site and an AatII restriction site. The 100 base pair PCR product was named EFp6.

Thus, upon ligation of the 3' end of ABNC PCR product to the 5' end of EFp6 PCR product the protease cleavage site is reconstituted between NC and p6. Similarly, ligation of the EFp6 PCR product to the CDPR PCR product reconstitutes the same protease cleavage site between p6 and PR.

The DNA sequence of each primer was:

```
primer A, NC:
                                        (SEQ ID NO: 1)
5'-CGAAGGAGGTCCCAACTCGA-3' primer B, NC:
                                        (SEQ ID NO: 2)
5'-CGATTGTTAACTCTAGAGTCAGGAGGGAGGTCTGGGGTCTTG-3' primer C, PR:
                                        (SEQ ID NO: 3)
5'CGATTCGATCGCCCCAGACGTCCCTCCTGACCCTAGATGACTAGGGAG

GT-3' primer D, PR:
                                        (SEQ ID NO: 4)
5'-ACGGGGGTAGAGGTTGCTTT-3' primer E, p6:
                                        (SEQ ID NO: 5)
5'-TGACTCTAGATGACCCAGAGCCAACAGCCCCACCAGAAGAGAGCT

T-3' primer F, p6:
                                        (SEQ ID NO: 6)
5'-GCATTGTTAACGACGTCTCGCTGCCAAAGATCTGCGGGAAGCTAAA

GGATACAG-3'
```

The second step of cloning consisted of inserting CDPR into the SK-Ceb plasmid (FIG. 3B.1). The CDPR PCR product was digested with PvuI and BclI. The KS-Ceb plasmid was digested with XhoI and PvuI to produce a 560 bp fragment and with BclI and XbaI to produce a 2589 bp fragment. The three fragments were then ligated into SK-Ceb vector digested with XhoI and XbaI, generating the SK-Ceb-CDPR cloning intermediate.

The third step (FIG. 3B.2) involved the insertion of the other two PCR products, ABNC and EFp6, into the SK-Ceb-CDPR plasmid. The ABNC PCR product was digested with PvuI and XbaI and the EFp6 with XbaI and AatII. The two fragments were mixed with the XhoI-PvuI fragment from SK-Ceb (FIG. 3B.1) and then ligated into the SK-Ceb-CDPR plasmid, digested with XhoI and AatII. The DNA sequence of this cloning intermediate, referred to as KS-Ceb-p6 was verified by DNA sequencing.

Finally the XhoI-SacII fragment from SK-Ceb-p6, containing the p6 sequence, was cloned into the original Ceb expression plasmid resulting in the construct named Ceb-p6, depicted in FIG. 3C.

To construct the chimera containing the p6 mutant the p6 sequence was amplified using primers E and F2. The F2 primer is identical to the F primer except that it introduces a single nucleotide change which results in the change of amino acid Leu 44 to Phe. The PCR product was digested with XbaI and AatII, mixed with the XhoI-XbaI fragment containing ABNC from SK-Ceb-p6 and ligated into the SK-Ceb-CDPR, digested with XhoI and AatII. The DNA sequence was confirmed by sequencing. The p6L/F containing fragments was then cloned into the Ceb plasmid using the XhoI and SacII sites as with Ceb-p6. This plasmid was named Ceb-p6L/F.

A1.2. Cell Lines.

The TELFBASAF cell line was used for transfections of the wild-type and chimeric Ceb plasmids (Cosset et al., 1995b). This cell line consists of a polyclonal cell population derived from TE671 cells after phleomycin selection and expresses an amphotropic retroviral envelope and a retroviral lacZ vector. The amphotropic envelope expression plasmid consisted of the sequence coding for the 4070A envelope glycoprotein and a phleomycin resistance marker. The lacZ vector has been previously described (Ferry et al., 1991).

TE671 cells used for infection assays are human rhabdomyosarcoma cells (ATCC CRL 8805).

All cells were grown in DMEM (Life-Technologies) supplemented with 10% fetal bovine serum (Life-Technologies).

A1.3. Transfection and Selection.

For each plasmid, Ceb, Ceb-p6L/F and Ceb-p6, 3 μg/well were transfected by calcium precipitation (Cosset et al., 1995b) into TELFBASAF cells, seeded at 30% confluence in six-well plates. Cells were grown for 48 hours and then harvested, diluted and placed under blasticidine selection (36 μg/ml). Colonies were observed after three weeks at which point they were pooled. Cells were subsequently cultured in normal medium supplemented with blasticidine (36 μg/ml) and phleomycin (10 μg/ml). The process was repeated and three different series of polyclonal cell populations were established.

A1.4. Immunoblot Analysis.

Virus producer cells were harvested with versene (Life Technologies) washed with PBS and lysed in a 20 mM Tris-HCl buffer (pH 7.5) containing 1% Triton-X100, 0.05% SDS, 5 mg/ml sodium deoxycholate, 150 mM NaCl, and 1 mM PMSF. Lysates were incubated for 10 min at 4° C. and were centrifuged for 10 min at 10,000×g to pellet the nuclei. Supernatants were then frozen at −70° C. until further analysis. Virus samples were obtained by ultracentrifugation of culture supernatants (5 ml) in a SW41 Beckman Rotor (30,000 RPM, 1 hr, 4° C.). Pellets were suspended in 50 μl of PBS (phosphate buffered saline), and frozen at −70° C.

Samples (30 μg for cell lysates, or 20 μl for purified viruses) were mixed 5:1 (vol:vol) in a 375 mM Tris-HCl (pH 6.8) buffer containing 6% SDS, 30% β-mercapto-ethanol, 10% glycerol, and 0.06% bromophenol blue, boiled for 3 min, then run on 10% SDS acrylamide gels. After protein transfer onto nitrocellulose filters, immunostaining was performed in TBS (Tris buffered saline, pH 7.4) with 5% milk powder and 0.1% TWEEN. The blots were probed with the relevant antibody and developed using HRPO-conjugated Ig (immunoglobulins) raised against the species of each primary antibody (DAKO, UK) and an enhanced chemiluminescence kit (Amersham Life Science).

The anti-CA (Quality Biotech Inc, USA), a goat antiserum raised against the Rauscher leukemia virus p30 capsid protein (CA), was used diluted 1/10,000.

A1.5. Infection Assays.

Virus-containing supernatants were harvested after overnight production from freshly confluent Gag, Gag-p6L/F or Gag-p6 expressing cells, from the three different series of stables. Target TE671 cells were incubated with serial dilutions of the viral supernatant for 3-5 hours in the presence of polybrene (4 μg/ml). Infected cells were grown for 48-72 hours and stained for β-galactosidase expression.

A2. Results

A2.1. Establishment of Packaging Cell Lines Using Ceb-p6 Expression Plasmids.

The Ceb-p6, Ceb-p6L/F as well as the original Ceb expression plasmids were transfected into the TELFBASAF cell line, expressing the amphotropic MLV envelope and an nlslacZ retroviral vector. Following transfection, blasticidine resistant cells were pooled. Three independent series of stable producers were generated.

Figure 4:
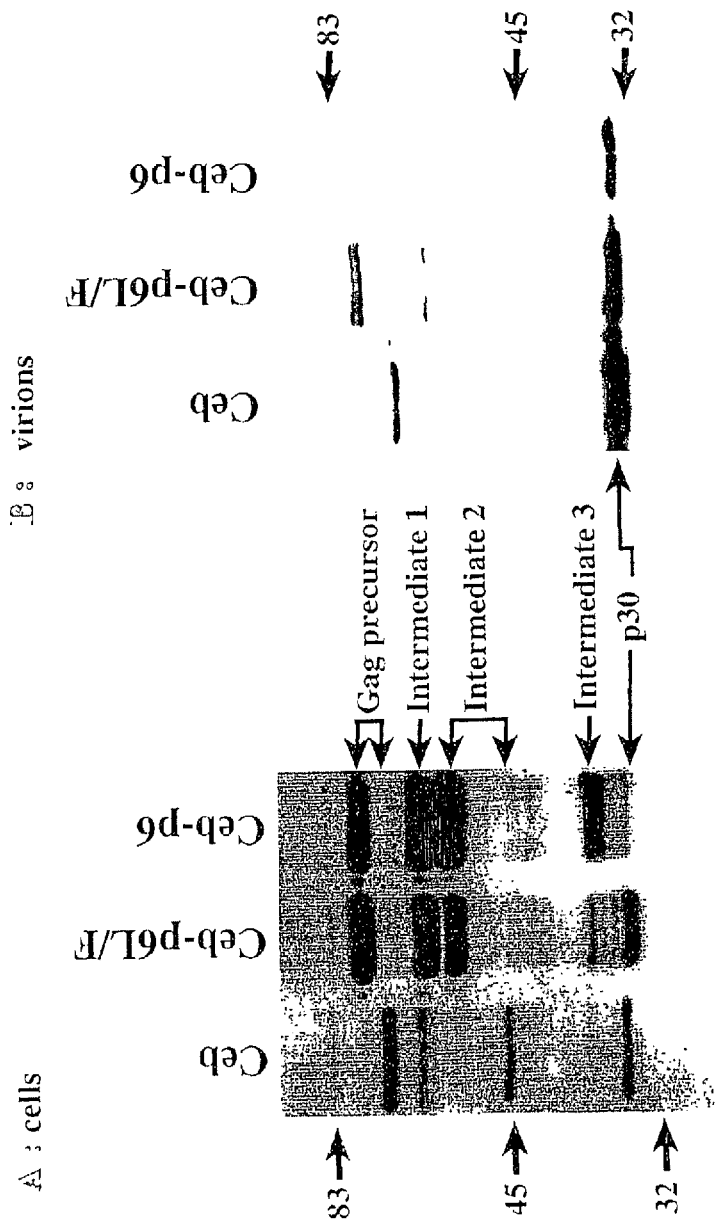

Expression of the chimeric Gag-p6 proteins was determined by immunoblot analysis of the cell lysates, using a polyclonal goat serum against the p30 capsid protein (FIG. 4A). This serum interacts with both the fully processed p30 as well as with the Gag precursor and any processing intermediates that contain p30. The results obtained using the polyclonal cell population series 2 are shown in FIG. 4, but similar results were obtained with the other series. The expression of the Gag precursor in cells transfected with Ceb-p6 and Ceb-p6L/F was higher than that obtained in Ceb transfected cells. As expected, the Gag-p6 and Gag-p6L/F precursors migrated more slowly than the Ceb precursor. The size difference corresponds to the size of p6 confirming the presence of this protein in the Gag precursor.

A band migrating closely to the wild-type MLV Gag precursor was also observed, intermediate 1. A similar band, but fainter, was observed with the wild-type MLV Gag. This band could correspond to processing intermediate of Gag, lacking NC and p6, that is more abundant in the case of the MLV Gag-p6 chimeras.

A difference in size between other processing intermediates was observed. In wild-type Ceb, a band was obtained that migrates close to 45 kD, intermediate 2. In the case of the Ceb-p6 and Ceb-p6L/F this band increased in size, suggesting that p6 remains associated with this intermediate. From the estimated size of the band, this could correspond to a cleavage product containing CA-NC in the case of the wild-type MLV Gag and CA-NC-p6 in the case of the MLV Gag-p6 chimeras.

Finally, the level of fully processed intracellular capsid p30 protein was similar in the case of wild-type Gag and chimeric Gag-p6L/F but reduced in the case of the Gag-p6 chimera. For the latter chimera, a band migrating slower more intense than in the other samples, intermediate 3. The size of the band corresponds to a product containing to CA and NC domains since it is also obtained with wild-type Gag at lower levels (see discussion).

Overall the data suggest that the presence of p6 does not interfere with Gag precursor expression, however, p6 seems to enhance processing of the Gag precursors within the cells.

A2.2. Retroviral Particle Formation.

The production of retroviral particles was analyzed by immunoblot analysis of the pellets obtained after ultracentrifugation of the supernatant from producer cells, using the anti-p30 antibody (FIG. 4B). Virion production from cells expressing Gag-p6L/F was reduced by about 2 fold as compared to that from wild-type Gag expressing cells. The yield of virions obtained from the Ceb-p6 expressing cells was further reduced. This is unlikely to reflect a processing defect in the two chimeras within the virions since their processing within cells is enhanced. Indeed, as the processing intermediates of the Gag-p6 chimeras observed in cell lysates are more abundant than those of wild-type Gag (FIG. 4A), the reduced virion yield could be due to premature processing inside the cell.

The virion yield obtained using the Gag-p6 chimeras was lower than the wild-type Gag but readily detectable (FIG. 4B), suggesting that the insertion of p6 into the MLV Gag was successful, in that it did not inhibit particle formation. Furthermore the virions produced are fully processed.

A2.3. Infectivity of the Chimeric Retroviruses.

To determine whether the produced retroviral particles were infectious, infection assays were carried out on TE671 cells expressing the PiT-2 amphotropic MLV receptor. Results obtained with the three different series of stable cell lines are shown (Table 1).

TABLE 1

Infections assays for retroviruses produced from TELFBASAF cells stably expressing Ceb, Ceb-p6L/F or Ceb-p6 plasmids.

| stable polyclonal | Plasmid expressed in TELFBASAF cells | | |
|---|---|---|---|
| cells | Ceb | Ceb-p6L/F | Ceb-p6 |
| series 1 | >$10^6$ | $1.4 \times 10^4$ | $3 \times 10^3$ |
| series 2 | >$10^6$ | $4 \times 10^4$ | $2 \times 10^4$ |
| series 3 | $4 \times 10^6$ | $2.5 \times 10^5$ | $1.9 \times 10^5$ |

Infection assays on TE671 cells. Titers as lacZ i.u./ml. For details see Materials and Methods.

The retroviruses produced from cells expressing the chimeric Gag proteins were infectious with titers reaching the order of $10^5$ i.u./ml. On average Gag-p6 expressing cells produced 2 fold lower titers of virus than did Gag-p6L/F expressing cells. In turn viruses from the Ceb-p6L/F expressing cells produced lower titers than did Ceb expressing cells. This difference varied between the different series and was associated with the level of Gag or Gag-p6 expressed in the cells. It is likely that, as polyclonal cell populations were studied, these differences arise due to variation between the total amount of Gag-expressing cells in each series. The differences in titer between each of the chimeric Gag virions and the wild-type Gag virions correlates with the difference in the levels of p30 detected in immunoblots. Therefore, if p6 is associated with the MLV virions, it does not interfere with their infectivity.

A3. Discussion

These results demonstrate that it is possible to insert small proteins into the MLV Gag-Pol precursor without inhibiting processing and assembly into infectious particles. Specifically, an (MLV) Gag-(HIV-1) p6 chimera was efficiently expressed and proved capable of assembling into virions. The proteolytic processing by the viral protease after virion budding proceeds normally, as shown by the immunoblot analysis on purified virions, and by the infectivity of these particles.

The Intracellular Processing of the Gag-p6 Chimeras is Enhanced Compared to that of Wild-Type MLV Gag.

The quantity of virions produced using the Gag-p6 chimeras was lower than that using the wild-type Gag which correlates with the decreased infectious titers obtained. This could be due to the enhanced premature processing of the chimeric Gag precursors within the cell, as judged by the abundance of processing intermediates in the cell lysates compared to those obtained with the wild-type MLV Gag. The exact mechanism of retroviral protease activation is not known, although it is linked to assembly and budding (see general introduction). It has been shown that when the Gag-Pol precursors are overexpressed in cells, premature processing is induced resulting in lower virus yields (Karacostas et al., 1993; Park and Morrow, 1991). Since the Gag-p6 precursors are expressed in higher amounts than the wild-type MLV Gag proteins, this could account for the increased intracellular processing observed.

In HIV-1 full length clones, p6 has been shown to be required for efficient particle release (Gottlinger et al., 1991; Huang et al., 1995). p6 appears to act late during budding and its effect is linked to the viral protease function (Huang et al., 1995). Indeed, inactivation of the HIV-1 protease by mutagenesis (Huang et al., 1995) or expression of HIV-1 Gag in the absence of other viral proteins (Lu et al., 1993; Paxton et al., 1993; Royer et al., 1991), alleviated the requirement of p6 for budding. In this example, the MLV protease was active and thus, it might be possible that p6 has an effect on MLV protease as it does in the HIV-1 context (Huang et al., 1995). Alternatively, fusion of p6 to the MLV Gag precursor might affect the conformation of the polyprotein, thereby altering its processing by the viral protease. Likewise, in the context of HIV-1, Gag removal or mutagenesis of p6 has been suggested to change the Gag protein conformation (Royer et al., 1991).

Although both the Gag-p6 and Gag-p6L/F precursors exhibit similar amounts of intracellular processing, certain processing intermediates appear more abundant in the Gag-p6 context as compared to the Gag-p6L/F. Processing of the Gag precursor proceeds in an ordered manner, dictated by the amino acid sequence differences at the cleavage sites and their accessibility to the viral protease (Pettit et al., 1994; Tritch et al., 1991). Effects on the order of processing were also observed in HIV-1 Gag, where mutagenesis of p6 resulted in a reduced rate of cleavage between certain Gag proteins (Huang et al., 1995). This observation is compatible with an effect of p6 either directly on the protease or on Gag precursor conformation that, in turn, alters processing. Mutations within the HIV-1 and RSV Gag precursor that alter the order of processing of the protein result in reduced particle release (Bowles et al., 1994; Tritch et al., 1991). Thus, modified processing of the Gag-p6 protein precursor could explain the even lower particle yield of the Gag-p6 compared to the Gag-p6L/F. Thereby, mutation of the p6 Leu44 to Phe appears to modify the effect of p6 on the cleavage of the MLV Gag. In contrast, mutations in this region of p6 in the context of HIV-1 Gag, had little or no effect on particle release and the 'effector' region was identified at the N-terminus of p6 (Huang et al., 1995).

The enhanced intracellular processing of Gag-p6 is useful in determining the sequence of the Gag precursor cleavage events, based on size differences between intermediates containing p6 and the wild-type Gag equivalents. In agreement with previously reported findings (Maxwell and Arlinghaus, 1981; Yoshinaka and Luftig, 1982), the pp12-CA site appears to be processed early during assembly and budding (Intermediate 2, FIG. 4). The CA N-terminus was also reported to be rapidly processed in other viruses, such as HIV-I and RSV release (Tritch et al., 1991; Bowles et al., 1994). The increased and potentially modified processing of the Gag-p6 polyprotein reveals a processing intermediate that is present only at a very low level in the wild-type MLV Gag context (Intermediate 3, FIG. 4). The size of this product corresponds to a polypeptide containing CA and part of NC, or part of CA and part of NC. Previous studies have identified a product containing both CA and NC epitopes within purified MoMLV viral particles (Meyer et al., 1995). The site of cleavage appears to lie within the C-terminus of CA, upstream of the CA-NC junction (Meyer et al., 1995). Although the size of the product found in those studies was lower (about 12KD), than the product we observe (about 34KD), the presence of both products appears associated with high activity of the viral protease which suggests that they are present late in budding. Thus the 31KD protein observed here might be the result of activation of an alternative protease cleavage site within CA or NC or both. It would be interesting to determine whether we also obtain a 12KD intermediate. We will perform further immunoblot analysis using antibodies recognizing other Gag proteins, such as NC and MA, so as to determine in more detail the composition of the different intermediates observed.

Other Possible Effects of p6 on MLV Particle Assembly.

It has been recently reported that mutations within HIV-1 p6 affected envelope glycoprotein incorporation into particles (Ott et al., 1999). Although we have not confirmed the total amount of the MLV envelope glycoprotein in the Gag-p6, Gag-p6L/F derived particles as compared to the wild-type Gag equivalent, we think it is unlikely that p6 affects the amphotropic envelope incorporation. Firstly, in the same study (Ott et al., 1999) the p6 mutants could be complemented with envelope glycoproteins from VSV and MLV but not by a truncated HIV-1 envelope, showing that the effect was specific for HIV-1 glycoproteins. Secondly, the reduced infectious titers obtained with the Gag-p6 derived particles correlate well with the reduced amounts of total virion production as determined by immunoblots using the anti-CA serum. Thus, it is likely that presence of p6 in the MLV Gag precursor does not affect the incorporation of the MLV envelope glycoprotein into the virions, although immunoblot analysis is required to conclude this definitely.

Recent studies have shown than ubiquitin is covalently attached to the p6 protein of HIV and SIV Gag precursors (Ott et al., 1998). Ubiquitin was also detected in MLV virions associated with the pp12 protein (Ott et al., 1998), as well as ALV particles, although it was not found to be associated with ALV Gag (Putterman et al., 1990). The role of this protein in virions has not been determined but its association with p6 raises the possibility that it might be involved in late steps of assembly and budding (Ott et al., 1998). In the chimeric Gag-p6 construct the presence of both pp12 and p6 proteins might increase the ubiquination of the Gag-p6 precursor and this might also interfere with budding of the chimeric virions.

Other Gag-Peptide/Nucleic Acid Fusions.

Although this example discloses specifically the incorporation of a p6 peptide in the MLV synthetic retroviral particle, the teaching of the invention is more general and provides a novel approach to incorporate peptides, polypeptides or nucleic acids into viral particles. In this regard, any nucleic acid encoding a peptide or polypeptide of between 3 and 100 amino acids, even more preferably between 3 and 70 amino acids can be inserted in the gag-fusion of this invention. Also, as indicated above, the fusion may contain a protease cleavage site, to release to inserted polypeptide sequence upon expression of the fusion molecule, or may not contain such a site.

B—Use of a Synthetic Retroviral Particle to Produce an Immune Response In Vivo The immunogenicity of synthetic retroviral particles presenting a synthetic viral envelope protein has been demonstrated in vivo, following injection thereof into mice. The synthetic envelope protein is the glycoprotein (GP) of the LCMV virus, whose principal epitope is the GP33-41 epitope, presented by the histocompatibility molecules H-2D$^b$. The particles immunogenicity has been determined in CR-transgenic C57BL/6 mice (H-2D$^b$), whose CD8 T lymphocytes express a T receptor (TCR Vα2 V138) specific for the GP33-41 epitope. The activation status of the transgenic CD8 T lymphocytes has been measured on the basis of CD44 (Pgp-1) and CD45RB surface markers expression. In the GP-LCMV retrovirus-infected mice, the GP33-41-specific T lymphocytes present a phenotype characteristic of effector cells (expressing both the CD44 and CD45RB markers at high levels), seven days post infection.

The synthetic retroviral particles have been produced from the packaging cell line H293-341-LCMV.GP. H293-341-LCMV.GP derives from the human embryonic kidney cell line H293 (ATCC: CRL-1573) by transfection with plasmid pNp3189 containing the Moloney (Mo-MLV) Gag and Pol coding sequences, then with plasmid phCMV-LCMV.GP; and selection for resistance to both blasticidine and neomycine. The selected clones were cultured in production media (DMEM), free of serum, for 24 hours, and the supernatant was collected and filtered, prior to injection.

Figure 6:
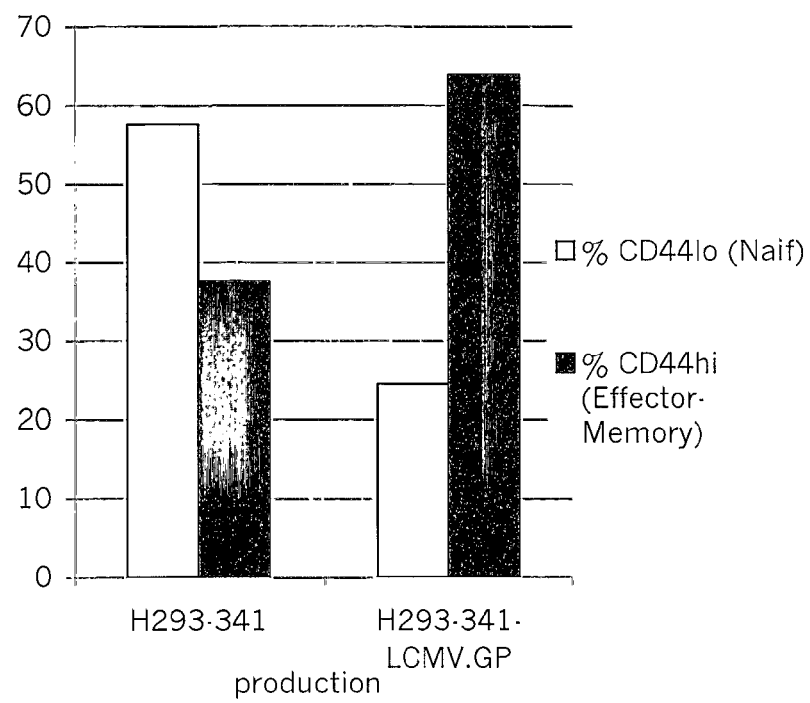

In this experiment, 500 μl of non-concentrated supernatant have been injected intraperitoneally into 2-3 weeks old TCR-transgenic mice. Control mice received injection of supernatant of clones H293-341. Seven days post injection, blood and spleen samples were collected, immunolabeled (using $2.10^6$ cells), and analysed by flux cytometry. The percentages of cells having a naïve (CD44$^{lo}$ CD45RB$^{hi}$) effector (CD44$^{hi}$ CD45RB$^{hi}$) or memory (CD44$^{hi}$ CD45RB$^{lo}$) phenotype have been determined and are disclosed in the Table 2 below for the CD8$^+$ TCR Vα2 T cell population (see also FIG. 6.

TABLE 2

| Production | CD8$^+$ TCR Vα2 T cells phenotype | |
|---|---|---|
| | CD44$^{lo}$ (naïve) | % CD44$^{hi}$ effector-memory |
| H293-341 | 57.6 | 37.6 |
| H293-341-LCMV.GP | 24.5 | 63.9 |

These results show that the synthetic retroviral particles presenting at their surface the synthetic LCMV glycoprotein have the ability to induce an immune response in vivo, directed against the viral GP33-41 epitope, efficiently recognized by corresponding Ag-specific T cells.

C—Immunogenic Composition Comprising a Modified Envelope Protein

Figure 7:
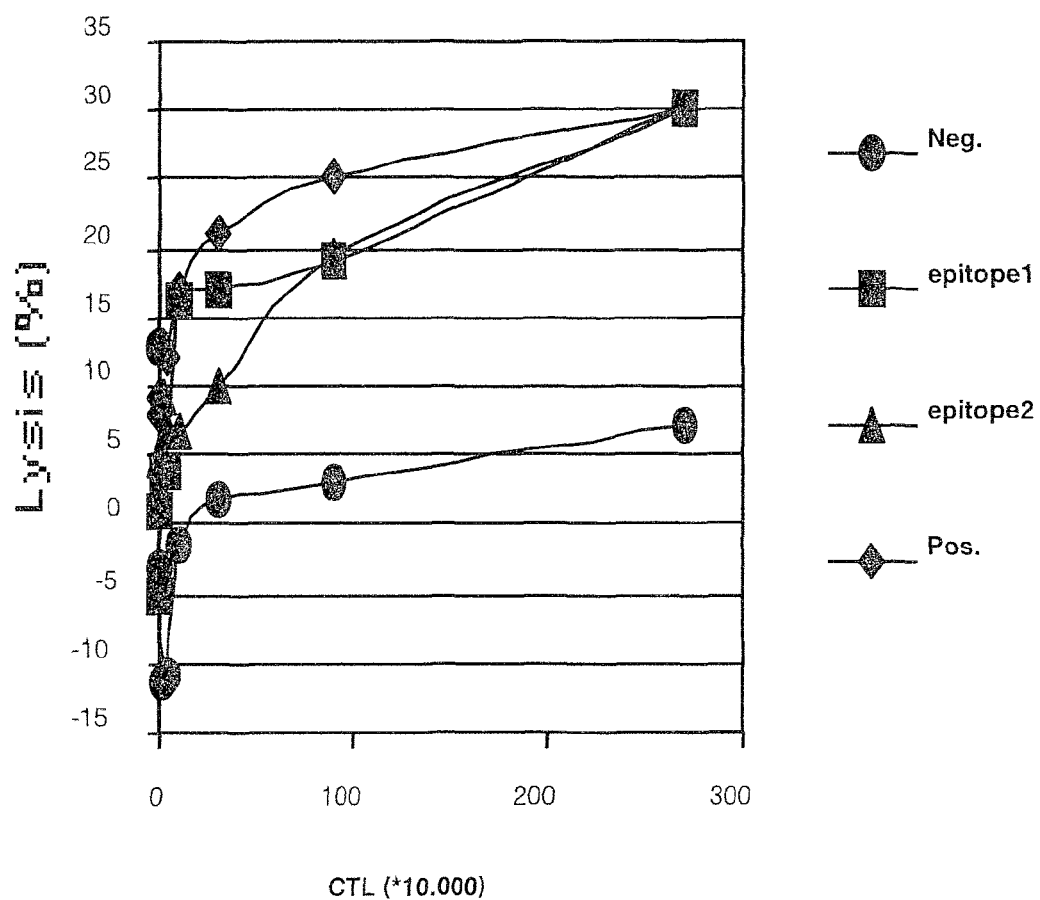

The dominant epitope GP$_{33-41}$ of the LCMV env was subcloned into the amphotrope MLV env 4070A. The recombinant plasmid comprising this chimeric envelope gene with the inserted LCMV epitope was transfected into the fibroblast cell line MC57. Proper expression and presentation of the epitope was assayed in a cytotoxic T-lymphocyte (CTL) assay. For that purpose, a mouse was immunized with the above peptide epitope and, at day 3, the spleen cells were collected for the CTL assay. The CTLs were mixed with the transfected fibroblasts, and lysis of target cells was measured. Negative and positive controls were assayed in parallel. The results presented on FIG. 7 show an effective lysis of epitope-presenting cells. This demonstrates, for the first time, that in this context an epitope incorporated into a retroviral envelope can be properly processed and recognized by the immune system.

The invention claimed is:

1. An immunogenic composition comprising a non-infectious synthetic retroviral particle comprising:
   a core comprising a polypeptide consisting of a self-assembling Gag protein of a particular retrovirus; and
   a lipid bilayer envelope comprising one or more selected peptide antigens heterologous to any retrovirus;
   wherein the one or more selected peptide antigens are exposed at the surface of the particle;
   wherein the non-infectious synthetic retroviral particle is devoid of any retroviral genome; and
   wherein the non-infectious synthetic retroviral particle is devoid of envelope protein of the particular retrovirus.

2. The immunogenic composition of claim 1, comprising at least about $10^2$ to about $10^9$ of the synthetic retroviral particles.

3. The immunogenic composition of claim 1, wherein the synthetic retroviral particle is devoid of envelope protein of any retrovirus.

4. The immunogenic composition of claim 1, wherein the particular retrovirus is an onco-retrovirus or a spumavirus.

5. The immunogenic composition of claim 4, wherein the particular retrovirus is not HIV.

6. The immunogenic composition of claim 1, wherein the one or more selected peptide antigen is a glycopeptide antigen.

7. The immunogenic composition of claim 2, wherein the one or more selected peptide antigen naturally comprises at least a portion of a transmembrane domain.

8. The immunogenic composition of claim 2, wherein the one or more selected peptide antigen comprises a synthetic peptide.

9. The immunogenic composition of claim 8, wherein the synthetic peptide is between 3 and 60 amino acids in length.

10. The immunogenic composition of claim 1, further comprising a pharmaceutically acceptable vehicle.

11. The immunogenic composition of claim 10, further comprising an adjuvant.

12. The composition of claim 1, wherein the composition induces an immune response to the one or more selected peptide antigens.

13. A method of stimulating an immune response in a subject, the method comprising steps of administering the immunogenic composition of claim 1 to a subject in need thereof.

14. The method of claim 13, wherein the immune response in the subject includes a humoral response.

15. The composition of claim 1, wherein the core consists of the polypeptide consisting of the self-assembling Gag protein.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer A, NC.

<400> SEQUENCE: 1
cgaaggaggt cccaactcga                                                    20

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic
      Primer B, NC.

<400> SEQUENCE: 2
cgattgttaa ctctagagtc aggagggagg tctgggtct tg                            42
```

```
<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence: Synthetic
      Primer C, PR.

<400> SEQUENCE: 3
cgattcgatc gccccagacg tccctcctga ccctagatga ctagggaggt          50

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer D, PR.

<400> SEQUENCE: 4 acggggtag aggttgcttt                                            20

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: Synthetic
      Primer E, p6.

<400> SEQUENCE: 5
tgactctaga tgacccagag ccaacagccc caccagaaga gagctt              46

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: Synthetic
      Primer F, p6.

<400> SEQUENCE: 6
gcattgttaa cgacgtctcg ctgccaaaga tctgcgggaa gctaaaggat acag     54

<210> SEQ ID NO 7
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
accucccucc ugacccuaga ugacuaggga ggucagdgguc aggagccccc c       51
```